(12) United States Patent
Lavallee et al.

(10) Patent No.: US 10,441,294 B2
(45) Date of Patent: Oct. 15, 2019

(54) SYSTEM FOR THE TREATMENT OF A PLANNED VOLUME OF A BODY PART

(71) Applicant: DePuy Ireland Unlimited Company, Ringaskiddy (IE)

(72) Inventors: Stephane Lavallee, St Martin D'uriage (FR); Matias De La Fuente Klein, Aachen (DE); Klaus Radermacher, Stolberg (DE); Annegret Niesche, Aachen (DE); Meiko Muller, Aachen (DE); Gregory Dez, Grenoble (FR); Herve Collet, Chatenay (FR)

(73) Assignee: DePuy Ireland Unlimited Company, Ringaskiddy (IE)

( * ) Notice: Subject to any disclaimer, the term of this patent is extended or adjusted under 35 U.S.C. 154(b) by 256 days.

(21) Appl. No.: 14/896,900

(22) PCT Filed: Jun. 11, 2014

(86) PCT No.: PCT/EP2014/062150
§ 371 (c)(1),
(2) Date: Dec. 8, 2015

(87) PCT Pub. No.: WO2014/198784
PCT Pub. Date: Dec. 18, 2014

(65) Prior Publication Data
US 2016/0113720 A1 Apr. 28, 2016

(30) Foreign Application Priority Data
Jun. 11, 2013 (EP) ..................... 13171546

(51) Int. Cl.
*A61B 17/15* (2006.01)
*A61B 34/10* (2016.01)
(Continued)

(52) U.S. Cl.
CPC ............ *A61B 17/154* (2013.01); *A61B 17/15* (2013.01); *A61B 17/17* (2013.01);
(Continued)

(58) Field of Classification Search
CPC ............ A61B 34/30; A61B 2034/2055; A61B 2034/104
(Continued)

(56) References Cited

U.S. PATENT DOCUMENTS 987,273 A    3/1911  Wardwell
4,586,497 A * 5/1986  Dapra ................ A61B 17/1671
                                                606/180

(Continued)

FOREIGN PATENT DOCUMENTS

CN    104688341 A   6/2015
DE    10353700 A1   6/2005
(Continued)

OTHER PUBLICATIONS

European Search Report, dated Oct. 24, 2013, European Application No. EP13171546.
(Continued)

*Primary Examiner* — David W Bates
(74) *Attorney, Agent, or Firm* — Nutter McClennen & Fish LLP

(57) ABSTRACT

The invention relates to a surgical system comprising:
(i) a handheld device (100) comprising:
  a base (1),
  an end-effector (2) for mounting a surgical tool or tool guide,
  an actuation unit (4) connected to said base (1) and end-effector (2),
  a support unit (5) designed to make contact with the treated part to be treated or an adjacent region to provide a partial mechanical link between the base (1) or end-effector (2), and the part to be treated,
(ii) a tracking unit (200),
(iii) a control unit (300) configured to:
  (a) compute in real time an optimized path of the end-effector, (Continued)

(b) detect whether said computed path of the tool or end-effector can be achieved without changing the pose of the base, and, if not, determine a possible repositioning of the base with respect to the part to be treated,
(c) configure the actuation unit so as to move the end-effector according to said computed path, and
(d) iterate steps (a) to (c) until the planned volume has been treated,
(iv) a user interface (400).

32 Claims, 13 Drawing Sheets

(51) Int. Cl.
  *A61B 34/00* (2016.01)
  *A61B 17/17* (2006.01)
  *A61B 34/20* (2016.01)
  *B25J 9/00* (2006.01)
  *B25J 15/00* (2006.01)
  *A61B 34/30* (2016.01)

(52) U.S. Cl.
  CPC .......... *A61B 17/1764* (2013.01); *A61B 34/10* (2016.02); *A61B 34/70* (2016.02); *B25J 9/0009* (2013.01); *B25J 15/0019* (2013.01); *A61B 17/1742* (2013.01); *A61B 2034/104* (2016.02); *A61B 2034/2051* (2016.02); *A61B 2034/304* (2016.02); *Y10S 901/09* (2013.01)

(58) Field of Classification Search
  USPC .......................................................... 606/130
  See application file for complete search history.

(56) References Cited

U.S. PATENT DOCUMENTS

| | | | |
|---|---|---|---|
| 5,806,518 A | 9/1998 | Mittelstadt | |
| 6,033,409 A | 3/2000 | Allotta | |
| 6,226,548 B1 | 5/2001 | Foley et al. | |
| 6,228,089 B1 | 5/2001 | Wahrburg | |
| 6,468,265 B1 | 10/2002 | Evans et al. | |
| 6,554,837 B1 | 4/2003 | Hauri et al. | |
| 6,757,582 B2 | 6/2004 | Brisson et al. | |
| 7,022,123 B2* | 4/2006 | Heldreth ............ A61B 17/1626 606/80 |
| 7,035,716 B2 | 4/2006 | Harris et al. | |
| 7,346,417 B2 | 3/2008 | Lueth et al. | |
| 7,643,862 B2 | 1/2010 | Schoenefeld | |
| 8,096,997 B2 | 1/2012 | Plaskos et al. | |
| 8,206,053 B2 | 6/2012 | Bennett et al. | |
| 8,347,755 B2 | 1/2013 | Bennett et al. | |
| 8,347,756 B2 | 1/2013 | Bennett et al. | |
| 8,357,165 B2 | 1/2013 | Grant et al. | |
| 8,366,719 B2* | 2/2013 | Markey ............ A61B 17/1626 606/104 |
| 8,460,277 B2 | 6/2013 | Suarez et al. | |
| 8,560,047 B2 | 10/2013 | Haider et al. | |
| 8,641,726 B2 | 2/2014 | Bonutti | |
| 8,753,346 B2 | 6/2014 | Suarez et al. | |
| 8,834,490 B2 | 9/2014 | Bonutti | |
| 8,838,205 B2 | 9/2014 | Shoham et al. | |
| 8,852,210 B2 | 10/2014 | Selover et al. | |
| 8,876,830 B2 | 11/2014 | Hodorek et al. | |
| 8,882,777 B2 | 11/2014 | Heavener et al. | |
| 8,961,500 B2 | 2/2015 | Dicorleto et al. | |
| 8,961,536 B2 | 2/2015 | Nikou et al. | |
| 8,961,537 B2 | 2/2015 | Leung et al. | |
| 8,965,485 B2 | 2/2015 | Balaji et al. | |
| 8,965,583 B2 | 2/2015 | Ortmaier et al. | |
| 8,992,534 B2 | 3/2015 | Lee et al. | |
| 8,992,542 B2 | 3/2015 | Hagag et al. | |
| 9,008,757 B2 | 4/2015 | Wu | |
| 9,033,958 B2 | 5/2015 | Mailloux et al. | |
| 9,060,794 B2 | 6/2015 | Kang et al. | |
| 9,084,613 B2 | 7/2015 | Qutub | |
| 9,101,443 B2 | 8/2015 | Bonutti | |
| 9,119,638 B2 | 9/2015 | Schwarz et al. | |
| 9,125,680 B2 | 9/2015 | Kostrzewski et al. | |
| 9,161,760 B2 | 10/2015 | Suarez et al. | |
| 9,173,716 B2 | 11/2015 | Kasodekar et al. | |
| 9,198,731 B2 | 12/2015 | Balaji et al. | |
| 9,220,510 B2 | 12/2015 | Cheal et al. | |
| D749,223 S | 2/2016 | Vargas et al. | |
| 9,259,278 B2 | 2/2016 | Jensen | |
| 9,308,050 B2 | 4/2016 | Kostrzewski et al. | |
| 9,342,632 B2 | 5/2016 | Zoran et al. | |
| 9,345,552 B2 | 5/2016 | Janik et al. | |
| 9,421,019 B2 | 8/2016 | Plaskos et al. | |
| 9,498,231 B2 | 11/2016 | Haider et al. | |
| 9,561,082 B2 | 2/2017 | Yen et al. | |
| 9,622,823 B2 | 4/2017 | Bozung et al. | |
| 9,707,043 B2* | 7/2017 | Bozung ............ A61B 17/32002 |
| 9,713,499 B2 | 7/2017 | Bar et al. | |
| 9,795,451 B2 | 10/2017 | Gorek et al. | |
| 9,814,468 B2 | 11/2017 | Kang et al. | |
| 9,979,859 B2 | 5/2018 | Manda | |
| 2003/0208122 A1 | 11/2003 | Melkent et al. | |
| 2004/0147920 A1* | 7/2004 | Keidar ................ A61B 5/06 606/34 |
| 2005/0020909 A1 | 1/2005 | Moctezuma de la Barrera et al. | |
| 2005/0149050 A1 | 7/2005 | Stifter et al. | |
| 2005/0171553 A1 | 8/2005 | Schwarz et al. | |
| 2006/0015114 A1 | 1/2006 | Bernardoni et al. | |
| 2006/0142657 A1 | 6/2006 | Quaid et al. | |
| 2006/0287733 A1 | 12/2006 | Bonutti | |
| 2007/0156157 A1 | 7/2007 | Nahum et al. | |
| 2008/0140081 A1 | 6/2008 | Heavener et al. | |
| 2008/0269596 A1 | 10/2008 | Revie et al. | |
| 2009/0287222 A1 | 11/2009 | Lee et al. | |
| 2011/0082587 A1 | 4/2011 | Ziaei et al. | |
| 2011/0196385 A1 | 8/2011 | Altrogge et al. | |
| 2011/0208196 A1 | 8/2011 | Radermacher et al. | |
| 2011/0262224 A1 | 10/2011 | McCandless et al. | |
| 2012/0053488 A1 | 3/2012 | Boutin et al. | |
| 2012/0071893 A1 | 3/2012 | Smith et al. | |
| 2012/0123418 A1 | 5/2012 | Giurgi et al. | |
| 2012/0143084 A1* | 6/2012 | Shoham ............ A61B 17/1675 600/567 |
| 2012/0237105 A1 | 9/2012 | Mielekamp | |
| 2013/0060278 A1 | 3/2013 | Bozung et al. | |
| 2013/0169423 A1 | 7/2013 | Iorgulescu et al. | |
| 2013/0172903 A1 | 7/2013 | Suarez et al. | |
| 2013/0296868 A1 | 11/2013 | Bonutti | |
| 2013/0345718 A1 | 12/2013 | Crawford et al. | |
| 2014/0073910 A1 | 3/2014 | Munrow et al. | |
| 2014/0107451 A1 | 4/2014 | Lee et al. | |
| 2014/0135791 A1* | 5/2014 | Nikou ................ A61F 2/4609 606/130 |
| 2014/0188134 A1 | 7/2014 | Nortman et al. | |
| 2014/0236159 A1 | 8/2014 | Haider et al. | |
| 2014/0276949 A1 | 9/2014 | Staunton et al. | |
| 2014/0282194 A1 | 9/2014 | Nikou et al. | |
| 2014/0316436 A1 | 10/2014 | Bar et al. | |
| 2015/0057675 A1 | 2/2015 | Akeel et al. | |
| 2015/0094736 A1 | 4/2015 | Malackowski et al. | |
| 2015/0100066 A1 | 4/2015 | Kostrzewski et al. | |
| 2015/0112344 A1 | 4/2015 | Shoham et al. | |
| 2015/0182285 A1 | 7/2015 | Yen et al. | |
| 2015/0202009 A1 | 7/2015 | Nussbaumer et al. | |
| 2015/0223897 A1 | 8/2015 | Kostrzewski et al. | |
| 2015/0245878 A1 | 9/2015 | Jaramaz et al. | |
| 2015/0245879 A1 | 9/2015 | Nikou et al. | |
| 2015/0289941 A1 | 10/2015 | Bowling et al. | |
| 2015/0305817 A1 | 10/2015 | Kostrzewski | |
| 2015/0366624 A1 | 12/2015 | Kostrzewski et al. | |
| 2016/0008011 A1 | 1/2016 | Kostrzewski | |
| 2016/0022374 A1 | 1/2016 | Haider et al. | |
| 2016/0030115 A1 | 2/2016 | Shen et al. | |
| 2016/0038238 A1 | 2/2016 | Kostrzewski et al. | |
| 2016/0081753 A1 | 3/2016 | Kostrzewski | |
| 2016/0081754 A1 | 3/2016 | Kostrzewski et al. | |

(56) References Cited

U.S. PATENT DOCUMENTS

| | | | |
|---|---|---|---|
| 2016/0128789 | A1 | 5/2016 | Kostrzewski et al. |
| 2016/0135816 | A1 | 5/2016 | Lavallee et al. |
| 2016/0135906 | A1 | 5/2016 | Cattin et al. |
| 2016/0206376 | A1 | 7/2016 | Haider et al. |
| 2016/0206377 | A1 | 7/2016 | Cheal et al. |
| 2016/0231734 | A1 | 8/2016 | Zoran et al. |
| 2016/0235492 | A1 | 8/2016 | Morard et al. |
| 2016/0310221 | A1 | 10/2016 | Bar et al. |
| 2016/0354168 | A1 | 12/2016 | Bonutti |
| 2017/0007327 | A1 | 1/2017 | Haider et al. |
| 2017/0071682 | A1 | 3/2017 | Bar et al. |
| 2017/0119421 | A1 | 5/2017 | Staunton et al. |
| 2017/0156799 | A1 | 6/2017 | Bozung |
| 2017/0245947 | A1 | 8/2017 | Bozung et al. |

FOREIGN PATENT DOCUMENTS

| | | |
|---|---|---|
| DE | 102014016823 A1 | 5/2016 |
| EP | 3130305 A1 | 2/2017 |
| KR | 10-2015-0005438 A | 1/2015 |
| KR | 10-2015-0138520 A | 12/2015 |
| KR | 10-1633774 B1 | 6/2016 |
| WO | 2005/048852 A1 | 6/2005 |
| WO | WO-2011133927 | 10/2011 |
| WO | 2012/068113 A1 | 5/2012 |
| WO | WO-2012109760 | 8/2012 |
| WO | 2012/131660 A1 | 10/2012 |
| WO | WO-2013052187 | 4/2013 |
| WO | WO-2014198784 | 12/2014 |
| WO | 2015/115807 A1 | 8/2015 |
| WO | 2015/115809 A1 | 8/2015 |
| WO | 2015/131138 A1 | 9/2015 |
| WO | 2016/049180 A1 | 3/2016 |
| WO | 2016/156168 A1 | 10/2016 |
| WO | 2016/156210 A1 | 10/2016 |
| WO | 2017/025607 A1 | 2/2017 |
| WO | 2017/122202 A1 | 7/2017 |

OTHER PUBLICATIONS

International Search Report and Written Opinion, dated Oct. 7, 2014, Application No. PCT/EP2014/062150.
International Search Report and Written Opinion, dated Oct. 9, 2014, Application No. PCT/EP2014/062165.
Bach, Christian M., et al., "No functional impairment after Robodoc total hip arthroplasty: Gait analysis in 25 patients", *Acta Orthop Scan*, 73(4), (Aug. 2002), 386-391.
Bargar, MD, William L., et al., "Primary and Revision Total Hip Replacement Using the Robodoc System", *Clinical Orthopaedics and Related Research*, No. 354, (Sep. 1998), 82-91.
Becker, Brian C., et al., "Handheld Micromanipulation with Vision-Based Virtual Fixtures", *IEEE International Conference on Robotics and Automation (ICRA)*, (May 9, 2011), 4127-4132.
Brisson, Gabriel, et al., "Precision Freehand Sculpting of Bone", *Proceedings of the 7th International Conference on Medical Image Computing and Computer-Assisted Intervention (MICCAI 2004)*, vol. 2, (2004), 105-112.
Cobb, J., et al,, "Hand-on robotic unicompartmental knee replacement: a prospective, randomised controlled study of the acrobat system", *The Journal of Bone & Joint Surgery (Br)*, vol. 88-B, No. 2, (Feb. 2006), 188-197.
Davies, BL, et al., "Robotic control in knee joint replacement surgery", *Proceedings of the Institution of Mechanical Engineers, Part H: Journal of Engineering in Medicine*, vol. 221, (Jan. 1, 2007), 71-80.
Dorr, MD, Lawrence D., et al., "Robotic Guidance in Total Hip Arthroplasty: The Shape of Things to Come", *Orthopedics | ORTHOSuperSite.com*, vol. 34, No. 9, (Sep. 2011), 652-655.
Kwoh, Yik San, et al., "A Robot with Improved Absolute Positioning Accuracy for CT Guided Stereotactic Brain Surgery", *IEEE Transactions on Biomedical Engineering*, vol. 35, No. 2, (Feb. 1988), 153-160.
Lavallee, S., "A New System for Computer Assisted Neurosurgery", *IEEE Engineering in Medicine & Biology Society 11th Annual International Conference*, (1989), 926-927.
Lieberman, MD, Isador H., et al., "Bone-Mounted Miniature Robotic Guidance for Pedicle Screw and Translaminar Facet Screw Placement: Part 1—Technical Development and a Test Case Result", *Neurosurgery*, vol. 59, No. 3, (Sep. 2006), 641-650.
Lonner, MD, Jess H., et al., "Robotic Arm-assisted UKA Improves Tibial Component Alignment: A Pilot Study", *Clinical Orthopaedics and Related Research*, vol. 468, (2010), 141-146.
MacLachlan, Robert A., et al., "Micron: An Actively Stabilized Handheld Tool for Microsurgery", *IEEE Transactions on Robotics*, vol. 28, No. 1, (Feb. 2012), 195-212.
Maeso, MD, MPH, Sergio, et al., "Efficacy of the Da Vinci Surgical System in Abdominal Surgery Compared with that of Laparoscopy: A Systematic Review and Meta-Analysis", *Annals of Surgery*, vol. 252, No. 2, (Aug. 2010), 254-262.
Mitchell, Ben, et al., "Development and Application of a New Steady-Hand Manipulator for Retinal Surgery", *IEEE International Conference on Robotics and Automation*, (Apr. 10, 2007), 623-629.
Plaskos, C., et al., "Praxiteles: a miniature bone-mounted robot for minimal access total knee arthroplasty", *Int J Medical Robotics and Computer Assisted Surgery*, vol. 1, No. 4, (Dec. 2005), 67-79.
Prymka, Marcel, et al., "The dimensional accuracy for preparation of the femoral cavity in Hip arthroplasty: A comparison between manual- and robot-assisted implantation of hip endoprosthesis stems in cadaver femurs", *Arch Orthop Trauma Surg*, vol. 126, (Jan. 2006), 36-44.
Strauss, G., et al., "Navigated control in functional endoscopic sinus surgery", *Int J Medical Robotics and Computer Assisted Surgery*, vol. 1, No. 3, (2005), 31-41.
Uneri, Ali, et al., "New Steady-Hand Eye Robot with Micro-Force Sensing for Vitreoretinal Surgery", *Proceedings of the 2010 3rd IEEE RAS & EMBS International Conference on Biomedical Robotics and Biomechatronics*, (Sep. 26, 2010), 814-819.
Yen, P-L, et al., "Active constraint control for image-guided robotic surgery", *Proceedings of the Institution of Mechanical Engineers, Part H: Journal of Engineering in Medicine*, vol. 224, (2010), 623-631.
Van Ham et al., "Machining and Accuracy Studies for a Tibial Knee Implant Using a Force-Controlled Robot", Computer Aided Surgery, vol. 3, Issue 3, 1998, pp. 123-133.
Siebert et al., "Technique and First Clinical Results of Robot-Assisted Total Knee Replacement", The Knee, vol. 9, Issue 3, 2002, pp. 173-180.
Serefoglou et al., "Path Planning with Collision Avoidance for 5-DOF Robotic Removal of Femoral Bone Cement in RTHR", 7th Annual Meeting of the International Society for Computer Assisted Orthopaedic Surgery, Heidelberg, Germany, Jun. 20-23, 2007, pp. 114-116.
Paul et al., "Development of a Surgical Robot for Cementless Total Hip Arthroplasty", Clin. Orthop. Relat. Res., vol. 285, Dec. 1992, pp. 57-66.
Lavallée et al., "A Technique for Accurate Transpedicular Screw Fixation Using CT Data and a 3-D Optical Localizer, Journal of Image Guided Surgery", Computer-Assisted Spine Surgery, vol. 1, No. 1, 1995, pp. 65-73.
International Preliminary Report on Patentability received for PCT Patent Application No. PCT/EP2014/062150, dated Dec. 23, 2015, 7 pages.
Heger et al., "Trackerless Ultrasound-Integrated Bone Cement Detection Using a Modular Mini-Robot in Revision Total Hip Replacement", Proceedings of the Institution of Mechanical Engineers, Part H: Journal of Engineering in Medicine, vol. 224, Issue 5, Oct. 8, 2009. pp. 681-690.
Brandt et al., "CRIGOS: a Compact Robot for Image-Guided Orthopedic Surgery," IEEE Transactions on Information Technology in Biomedicine, vol. 3, No. 4, Dec. 1999, pp. 252-260.
U.S. Appl. No. 14/986,898, filed Dec. 8, 2015, System for Positioning a Surgical Device.

(56) References Cited

OTHER PUBLICATIONS

International Preliminary Report on Patentability received for PCT Patent Application No. PCT/EP2014/062165, dated Dec. 23, 2015, 7 pages.

* cited by examiner

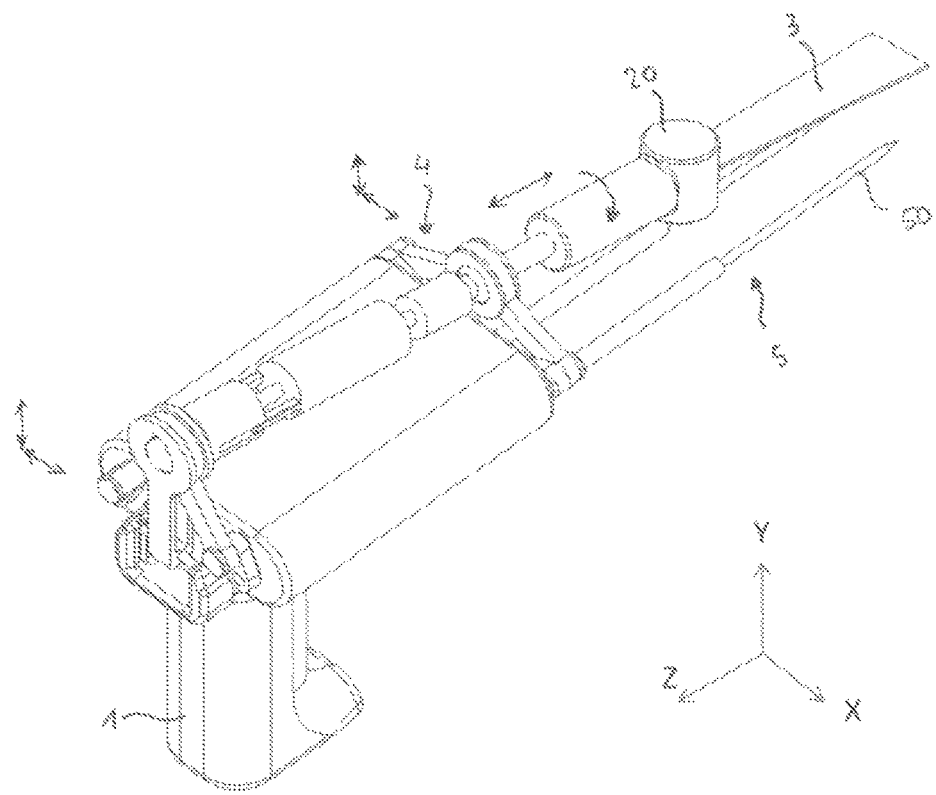
FIGURE 8C
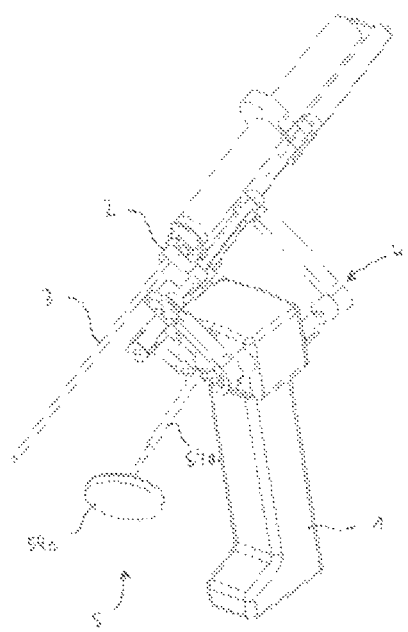 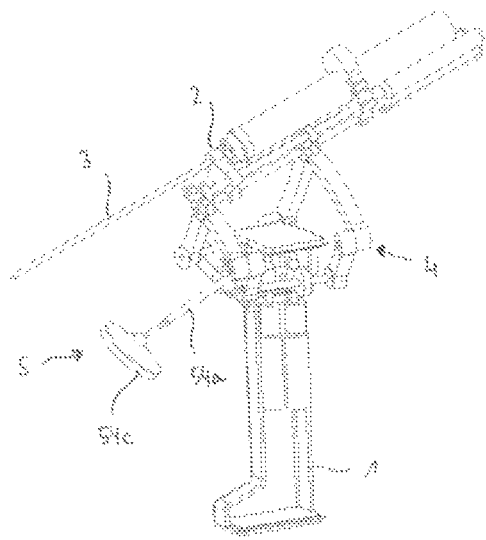
FIGURE 9A     FIGURE 9B

SYSTEM FOR THE TREATMENT OF A PLANNED VOLUME OF A BODY PART

FIELD OF THE INVENTION

The invention relates to a system for the treatment of a planned volume of a part of a patient's body.

BACKGROUND OF THE INVENTION

Robotic devices have been used in surgery since the late 1980s, beginning with a serial kinematic structured industry robot programmed to position a tool guide at a specified location near the head [Kwoh 1988] [Lavallée 1989]. During the 1990s, robots were introduced into orthopedic surgery with the ROBODOC system (ISS, USA) and the CASPAR (U.R.S., Germany) for hip and knee surgery [Bargar 1998, Prymka 2006]. However, not only did these autonomous systems not show more long term advantages than conventional techniques, they also showed longer operation times and increased blood loss [Bach 2002]. One of the disadvantages of these systems was the rigid fixation of the bone to the robot and the fully autonomous processing which took control away from the surgeon. Autonomous robots are not well-suited for soft-tissue surgery, as the shape of tissue may change when cut or pushed, or as a result of the patient's breathing.

Master-slave controlled robots, controlled via a console and remote visual feedback, have also been introduced [Maeso 2010]. The da Vinci system is used in minimally-invasive laparoscopic abdominal surgery, where the surgeon controls up to four robotic arms and the movements of the surgeon's hand can be filtered and scaled to enable precise instrument micro-movements.

In contrast to the da Vinci approach, where the surgeon controls the robot from a distance using a remote console, robots have also been introduced for cooperative work. These systems either position a tool guide and the surgeon itself guides the instrument [Liebermann 2006, Plaskos 2005], or the surgeon guides a haptic-controlled robot, and the robot prevents access to forbidden areas.

The concept of the haptic-controlled robot using "active constraints" or "virtual fixtures" was first implemented by the Acrobot system [Davies 2007, Yen 2010], and later by the MAKO Surgical Corp. RIO system. for UKA and THA [US 2006/0142657 A1 (Quaid et al.), Lonner 2010, Dorr 2011]. A randomized prospective study of the Acrobot system showed that with robotic bone preparation in UKA, the tibiofemoral alignment was within 2° of the planned position, whereas in the control group only 40% were below 2° [Cobb 2006].

A similar approach, but without using a huge robot system, is the use of "intelligent" high speed burrs that can be programmatically enabled and disabled in pre-planned areas. Whereas the Navigated Control concept controls the rotating speed of the burr [Strauss 2005], the Precision Freehand Sculptor comprises a burr that retracts behind a guard [Brisson 2004, WO 2011/133927 A2 (Nikou et al.)].

US 2005/0171553 (Schwarz et al.) discloses a handheld device for treating a body part that comprises a base, a tool that is able to move with respect to the base, and an actuation unit to move the tool within a predetermined working space to a predetermined position on the part to be treated. This device takes into account the movements of the base and of the part to be treated by detecting the position of the tool and the position of the part to be treated, by comparing said positions with a target position and by adapting the actuation unit accordingly. US 2012/0143084 (Shoham) describes a handheld device for treating a body part that comprises a handle, a tool that is able to move with respect to the handle, and a robot to move the tool within a predetermined working space to a predetermined position on the part to be treated. This device is able to detect the position of the tool with respect to a forbidden zone and to change the pose of the robot if the user moves the handle by an amount that would bring the tool within said forbidden zone. A disadvantage of these hand-guided tools is that the milling path itself needs to be controlled by the surgeon, which may result in non-efficient bone removal, inaccurate milling surfaces and unintended heat emission. In addition, significant time is required to obtain reasonable overall accuracy. Locally, milling surfaces are always bumpy or irregular, and to compensate for such bumps, cement is usually required between the milling surface and the implant, instead of non-cemented implants which are often preferred. Even with cement, the end result of such a process is an overall loss of accuracy.

For applications where no tremor is permitted, such as retinal surgery, a steady hand manipulator has been introduced [Mitchell 2007, Uneri 2010] as well as the handheld actively stabilized Micron device [Becker 2011, MacLachlan 2012].

US 2011/0208196 (Radermacher et al.) discloses a handheld reactive device for creating and applying constraints to the user that comprises a handle, a tool that is able to move with respect to the handle, and a support element connected to the handle by means of which the handle may be supported on a body surface. The support element is movable via an actuation unit which enables tool repositioning with respect to body surface by shifting the support element, based on sensor data obtained during the treatment. However, this device is applying constraints to the user depending on the material being worked, and it is not able to optimize the tool path actively in view of treating a planned volume of the body.

There remains a need for a lightweight, handheld surgical device which enables tool path optimization and compensation of the surgeon's small movements to minimize vibration and optimize accuracy.

BRIEF DESCRIPTION OF THE INVENTION

Accordingly, the invention provides a surgical system comprising:
  (i) a handheld device comprising:
    a base designed to be held in a user's hand,
    an end-effector for mounting a surgical tool, respectively a guide (20) for guiding a surgical tool, said surgical tool being designed to treat a planned volume of a part of a patient's body,
    an actuation unit connected to said base and said end-effector for moving said surgical tool, respectively tool guide, with respect to the base in order to treat said planned volume,
    a support unit connected to the base, respectively to the end-effector, comprising at least one element designed to make contact with the part to be treated or a region of the patient's body adjacent to the part to be treated so as to provide a partial mechanical link between the base, respectively the end-effector, and the part to be treated,
  (ii) a tracking unit configured to determine in real time the pose of at least one of the tool, the end-effector and the base with respect to the part to be treated, (iii) a control unit configured to:
  (a) compute in real time an optimized path of the tool or of the end-effector with respect to the base depending on said measured pose,
  (b) detect whether said computed path of the tool, respectively of the end-effector, can be achieved without changing the pose of the base, and, if this is not the case, determine a possible repositioning of the base with respect to the part to be treated,
  (c) configure the actuation unit so as to move the end-effector according to said computed path, and
  (d) iterate steps (a) to (c) until the planned volume has been treated,
(iv) a user interface configured to indicate feedback information to the user.

Advantageously, the feedback information provided by the user interface may comprise an indication of whether said computed path is achievable without changing the pose of the base and/or of the support unit with respect to the part to be treated, and, if not, an indication of a possible repositioning of the base and/or support unit determined by the control unit.

By "volume to be treated" is meant, in the present text, either a one-dimensional (1 D) volume that extends along a line (e.g. when the treatment consists in drilling a bore in the part), a two-dimensional (2D) volume that extends along a plane (e.g. when the treatment consists in sawing the part), or a three-dimensional (3D) volume (e.g. when the treatment consists in removing a predefined volume to match an implant perfectly or in removing a precise part that has been defined on images registered with the working coordinate system).

By "partial mechanical link" is meant a mechanical link between at least two parts, wherein a relative movement of said at least two parts in at least one degree of freedom is possible. This term excludes a "complete" mechanical link, i.e. a link wherein no relative movement between the parts is allowed (an example of such complete mechanical link would be attaching the base rigidly to the part to be treated (e.g. a bone) by at least one screw).

As described in further detail below, said partial mechanical link provided between the base and the part of the patient's body may be direct, meaning that the support unit is in contact with the part to be treated itself, or indirect, meaning that the support unit is in contact with a part of the patient's body adjacent to the part to be treated. Said adjacent part may consist of a bone belonging to the same joint as the part to be treated, or of soft tissues that surround the part to be treated. An indirect partial mechanical link may also be obtained when the support unit is held by a user's hand and that said hand leans onto the part to be treated or the soft tissues and skin surrounding the part to be treated.

Depending on the part with which the support unit makes contact and on the design of the support unit itself, said partial mechanical link may be rigid or damped.

The device is able to compensate for a given amount of pose errors (e.g. due to small movements of the user).

By "pose" is meant, in the present text, the 3D position and 3D orientation of a tool in up to six degrees of freedom. It is to be noted that depending on the application, it may not be necessary to determine all six degrees of freedom but only one or some of them.

By "path" is meant a set of tool poses that allow the planned volume to be treated.

A path is "optimized" if said set of poses is computed based on current relative poses of the device and of the part that remains to be treated, so as to minimize at least one of the following:
  number of necessary repositioning actions of the device to achieve the treatment;
  time needed to treat the planned volume;
  heat generated by the tool;
  surface roughness and accuracy of the treated part;
  orientation of the tool (or of cutting edges of a milling tool) with respect to the bone surface;
  (this list is not limitative).

According to advantageous but optional embodiments of the invention, taken alone or combined:
  a tool guide is mounted on the end-effector and the support unit comprises the tool guide;
  the support unit comprises at least one sensor for detecting a force exerted by the user on the partial mechanical link and the control unit is configured to check whether said force is greater than a threshold such that the support unit has a minimal damping parameter;
  the support unit comprises at least one damping element, such that said mechanical link created between the base or end-effector and the part to be treated is able to absorb reaction forces exerted by the treated part onto the tool.
  the damping characteristics of said at least one damping element are adjustable;
  the support unit comprises at least one pin having at least one rigid or damped degree of freedom;
  the support unit is designed as a second hand grip and the partial mechanical link between the patient and the manipulator is created via the second hand of the surgeon that holds the second hand grip;
  the support unit comprises at least one pad with a surface designed to adhere to patient soft tissue adjacent to the part to be treated;
  the support unit comprises a first portion connected to the base or the end-effector and a second portion intended to be fixed to the part to be treated or to a part of the patient adjacent to the part to be treated;
  the connection between the first and second portions of the support unit includes a hook-and-loop fastener or a magnetic fastener;
  the support unit comprises a hand grip that can be held by the other user's hand;
  the support unit is articulated with respect to the base;
  the surgical tool is articulated with respect to the end-effector;
  the control unit is configured to stop the actuation unit and/or the tool if said control unit detects that the current pose of the tool is outside of the planned volume;
  the support unit comprises a holding arm connected to the base of the handheld device and suited to be connected to a mechanical support such as an operating table;
  the support unit comprises a cable extending from a spring pulley and connected to the base of the handheld device, said spring pulley being suited to be connected to a mechanical support such as an operating table, ceiling of the room, fixed or mobile cart on the floor;
  the system comprises a planning system configured to determine a volume to be treated by the tool and, if appropriate, at least one processing parameter of the tool;
  a drill guide or a saw guide is comprised in the end-effector or in the support unit and the tool, which may or may not be a part of the device, is a drill or a saw that is intended to be moved within the axis or the plane of said guide;

the surgical tool comprises a saw, a drill, a mill, a shaver or a burr;

the tracking unit comprises at least one emitter and at least one sensor, said at least one emitter being mounted on the base or on the end-effector;

at least one sensor of the tracking unit is adapted to be mounted on the part to be treated.

According to an embodiment, the base of the handheld device is supported by a cable extending from a spring pulley.

The above-described system may be operated according to the process described below.

A handheld device is provided to a user, said handheld device comprising:

a base suited to be held in the user's hand, an end-effector for mounting a surgical tool, respectively a guide for guiding a surgical tool, said surgical tool being designed to treat a planned volume of a part of a patient's body, an actuation unit connected to said base and said end-effector for moving said surgical tool and/or tool guide with respect to the base in order to treat said planned volume, a support unit connected to the base, respectively to the end-effector, comprising at least one element suited to make contact with the part to be treated or a region of the patient's body adjacent to the part to be treated so as to provide a partial mechanical link between the base, respectively the end-effector, and the part to be treated.

Before starting the treatment one possibility is that first an optimal starting pose is calculated. A starting pose may be optimized concerning the following criteria:

maximum reachable part of the volume to be treated;

maximum distance of the volume to be treated to the limits of the robot workspace (if the entire volume is inside of the reachable robot workspace). The distance is important as to have maximum space where the robot can compensate for movements of the robot base;

orientation of the tool relative to the bone surface (the list is not limitative)

The user is then guided by the user interface to position the robot base in the optimal pose. To that end, different common graphical illustrations can be used such as lines, bars, crosses or 3D illustrations.

The user puts the support unit in contact with the part to be treated or a region of the patient's body adjacent to the part to be treated so as to provide a partial mechanical link between the base, respectively the end-effector, and the part to be treated.

The pose of at least one of the tool, the end-effector and the base with respect to the part to be treated is determined in real time by a tracking unit.

A control unit implements the following process:

(a) compute in real time an optimized path of the end-effector with respect to the base depending on said measured pose, (b) detect whether said computed path of the tool, respectively of the end-effector, can be achieved without changing the pose of the base, and, in the negative, determine a possible repositioning (new optimal starting position) of the base with respect to the part to be treated, (c) configure the actuation unit so as to move the end-effector according to said computed path, and (d) iterate steps (a) to (c) until the planned volume has been treated.

During operation of the tool, a user interface provides feedback information to the user; in particular, in an advantageous embodiment, the user interface indicates whether said computed path is achievable without changing the pose of the base and/or the support unit with respect to the part to be treated, and, in the negative, indicates a possible repositioning of the base and/or of the support unit determined by the control unit.

When a repositioning is necessary, it can be as for the starting position such that the robot and the tool are stopped and the user is guided until he reaches the optimal position and restarts the system, or it can be a continuous process such that during the repositioning into the direction of the new optimal position the process is not stopped.

BRIEF DESCRIPTION OF THE DRAWINGS

Other features, embodiments and advantages of the invention will be apparent from the detailed description that follows, based on the appended drawings wherein:

FIGS. 8A to 8C show an embodiment of a handheld device suited for total knee arthroplasty;

FIGS. 9A and 9B show an embodiment of a handheld device suited for the treatment of femoro-acetabular impingement;

DETAILED DESCRIPTION OF EMBODIMENTS OF THE INVENTION

The following description is focused on hip or knee surgery, in particular treatment of femoro-acetabular impingement (FAI), uni knee arthroplasty (UKA) and total knee arthroplasty (TKA).

The part to be treated is a bone such as the pelvis, the femur and/or the tibia, and the treatment consists in removing a planned volume of the bone.

However, the invention is not limited to these specific applications.

In particular, the part to be treated may not be a bone, and the treatment applied to said part may not imply removing a volume of said part.

For example, the device can be used for drilling, sawing, milling bones in any type of orthopaedic surgery performed to place various types of implants accurately (knee, hip, ankle, foot, wrist, shoulder, etc.) but also in laser surgery or radiofrequency ablation of soft tissues, sawing and milling bones in cranio-facial surgery, reshaping teeth to fit with inlays or onlays in dentistry, drilling holes to place dental implants, inserting screws in bones for traumatology, drilling tunnels for ligament reconstruction, performing one or multiple planar or dome osteotomies of bones, removing cement during a revision procedure, placing bone fragments accurately together, drilling inside the pedicles of vertebrae, removing cartilage defects, taking healthy parts of bone or cartilage in order to graft them, inserting inlays, implants, or grafts at precise locations, placing needles accurately during interventional radiology procedures, etc.

As will be explained in further detail below, the device is used in a context in which a volume of the part to be treated is planned before the surgical intervention.

Planning of the volume to be treated is performed using pre-operative images (e.g. CT, MRI, Ultrasound images, 3D X-rays, PET, etc.) or intra-operative 3D data (e.g. intra-operative CT, intra-operative MRI, Ultrasound images, 2D or 3D intra-operative X-ray images, geometric data provided by localizing systems and providing 3D points, clouds of 3D points, surfaces reconstructed from clouds of 3D points, etc.)), or both.

Multiple computer-assisted surgery methods are used to register the planned volume with a coordinate system attached to the part to be treated.

Typically, intra-operative images or data are used to register pre-operative images in a unique coordinate system attached to the part to be treated, and usually represented by a tracker (optical, magnetic, etc.).

Using any of these conventional computer-assisted surgery methods, the result is that the volume to be treated has a known geometric representation in a coordinate system attached to the part to be treated, and whose movements are tracked in real-time by a tracking unit as it will be detailed below.

As stated above, this volume may be a 1D, 2D or 3D volume depending on the application.

General Description of the Surgical System

Figure 1:
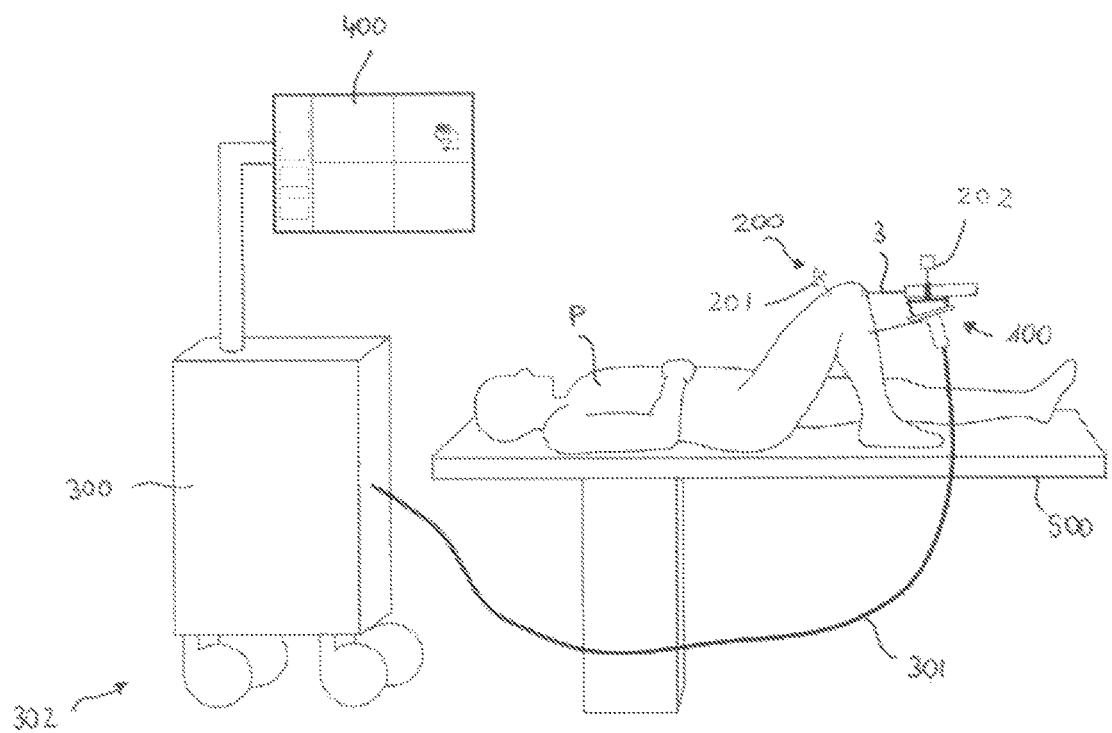
FIG. 1 shows an overview of a surgical system according to the invention.

FIG. 1 shows an overview of a surgical system according to the invention.

A patient P is lying on an operating table 500, e.g. in view of uni knee arthroplasty (UKA).

To that end, a tool 3 which is intended to remove a 3D volume from the tibial and femoral bones is supported by a handheld device 100 that is manipulated by a surgeon (not shown).

The handheld device 100 is connected to a control unit 300.

Said control unit typically comprises power supply, AC/DC converters, motion controllers to power the AC/DC motors of the actuation unit, fuses, real time control system interface circuits.

The system also comprises a tracking unit 200, such that the pose of the device and/or the bone to be treated is tracked in real-time and is shared between a real time control system and a planning system.

At least one coordinate system 201 is attached to the part to be treated while at least one coordinate system 202 is attached to the tool and/or the handheld device.

The tracking unit measures the relative motions between both coordinate systems 201, 202 at high frequencies.

The data obtained by the tracking unit are transferred to the control unit 300 via any suitable connection, with wires or wireless (not shown here).

The real time control system is able to carry out the proposed real time control algorithms at a reasonably high frequency.

Based on the volume to be removed and the previously removed volume and the actual pose of the device with respect to the bone to be treated, the real time control system calculates an optimal tool path.

There are many well-known algorithms in the robotics and machine literature for optimal milling path generation based on geometric information like binarisation of the volume to be removed, or iso-parametric path generation algorithms from numerical control machining.

In this figure, the connection is represented by a wire 301 but it may instead be wireless if the handheld device is battery-powered.

The control unit and tracking unit may be arranged in a cart 302 that can be moved in the operating room.

The system also comprises a user interface 400 that is intended to display feedback information to the surgeon and enables system configuration by the surgeon.

Said user interface 400 may advantageously comprise a screen located on the same cart 302 as the control unit and tracking unit.

In addition to or instead of said screen, the user interface may comprise an indicator that is arranged on the handheld device itself to provide information to the surgeon.

A surgical system wherein the control unit, tracking unit and/or user interface are embedded in the handheld device itself would still be within the scope of the invention, provided that the embedded units are powered by a sufficiently powerful battery and that their size and weight do not hinder the manipulation of the device by the user.

General Description of the Operation of the Surgical System

Before the surgical intervention, the user plans the intervention on the planning system, based on pre-operative and/or intra-operative medical images and data.

This planning step is conventional and will not be described in detail here.

It is specific to each application.

For example, in the case of TKA, planning of knee prosthesis on a femur requires definition of five cutting planes on the bone. In the case of FAI, planning of the volume to be removed on the femoral head and neck requires definition of a complex shape to be removed in order to retrieve a shape that has normal geometric parameters, such as the sphericity of the femoral head.

The planning system may form part of the surgical system according to the invention; otherwise, the planning system may be provided separately and connected to the control unit.

During the surgical intervention, the user may either use preoperative data/images together with intra-operative registration methods, or use directly intraoperative data/images.

In both cases, the result of the planning consists of at least one continuous volume to be treated by the tool, the pose of said volume to be treated being determined in the coordinate system of the part to be treated.

Said volume is then transferred to the control unit.

The control unit initializes its sub-systems and the device is ready to use.

Before the treatment starts, the support unit has to be connected to the part to be treated or an adjacent body part to provide a partial mechanical link between the device and the part to be treated.

Once the treatment has been started by the user, the control unit continuously feeds back status and tracking information to the planning system for recalculation and visualization purposes.

Figure 2:
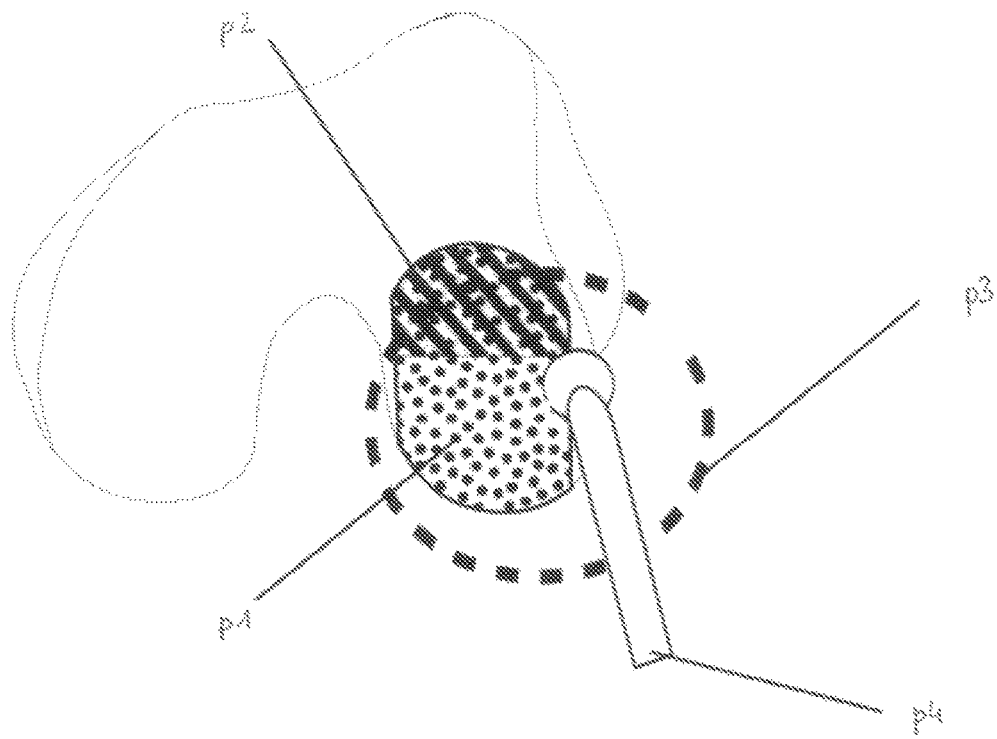
FIG. 2 illustrates planning details that can be displayed on a screen connected to the control unit.

FIG. 2 illustrates an example of planning details that may be displayed by the screen.

Part p1 shows the already treated volume whereas part p2 shows the volume that remains to be treated. Said remaining volume can be calculated by boolean mesh operations of the volume to be treated and the volume that already has been processed or by subtracting voxel volumes.

The dotted line p3 indicates the working space of the device, i.e. the space wherein the tool can be used to operate safely.

Due to the limited workspace of the device it may not be possible to treat the complete volume to be treated from one single pose of the device relative to the target volume. To inform the user which part of the volume to be treated can be safely treated from the current robot pose, the user interface can highlight that part of the volume that can be treated. The safely treatable part of the volume can be calculated by boolean mesh operations (or voxel volume subtraction) of the remaining volume to be treated and the robot workspace. To ensure that this part of the volume is "safely" removable, this calculation can also be done with a more limited sized volume of the device to be sure, the even at the border of the volume to be treated small deviations of the pose of the robot base are allowed.

This restricted workspace can be either calculated in the cartesian workspace by i.e. having an offset of several millimeters and degrees to the workspace limits, or in the axis space with a certain amount of encoder steps to the limits of each axis.

Part p4 is the tool pose with respect to the bone to be treated as measured by the tracking unit and/or calculated by the real time control unit.

During use of the handheld device, the user is provided with information regarding repositioning of the device to be carried out in order to maintain the tool in a predetermined working space.

According to the invention, the user benefits, on the one hand, from a free manipulation of base of the handheld device and, on the other hand, from the control unit's automatic tool path optimization.

The partial mechanical link provided by the support unit enables the surgeon to make small movements to reposition the device, without additional invasive action on the patient.

In addition, the user interface provides information to the user about the ability to treat the planned zone in the current device position and, if appropriate, gives indications on how to reposition the device appropriately.

The system ensures intervention safety as the control unit stops the tool if it leaves the planned working zone. In addition, the device's working space is small, providing inherent safety.

Another advantage of small working spaces is higher accuracy due to smaller leverages.

General Description of the Handheld Device

Figure 3A:
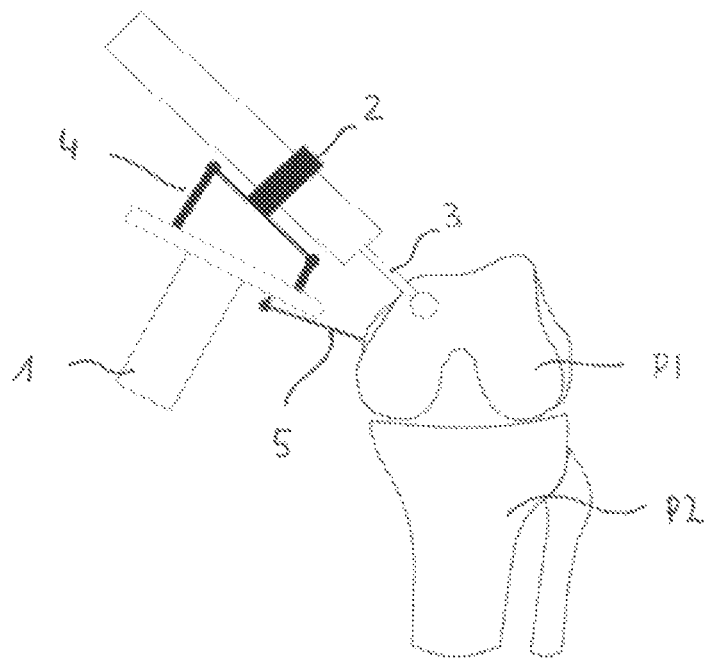
FIGS. 3A to 3L shows examples of embodiments of the handheld device and of the support unit.
Figure 3B:
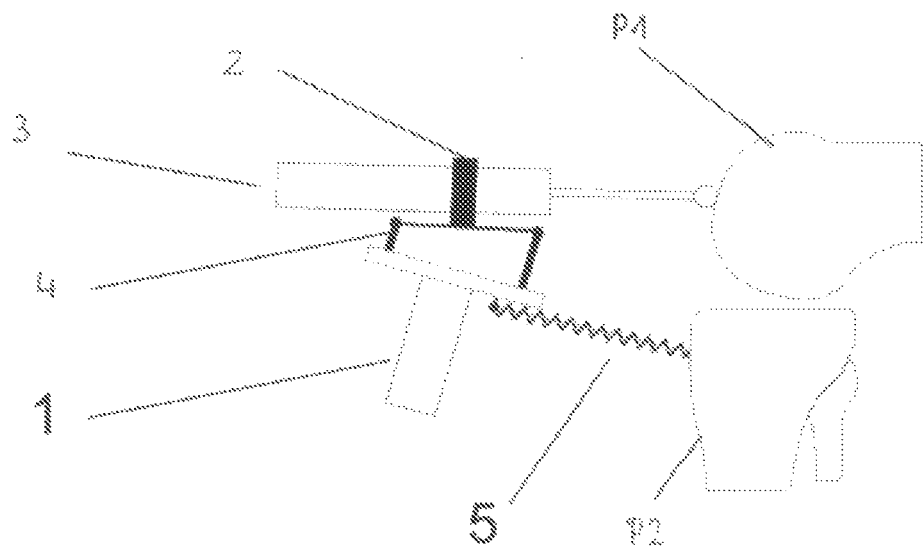
Figure 3C:
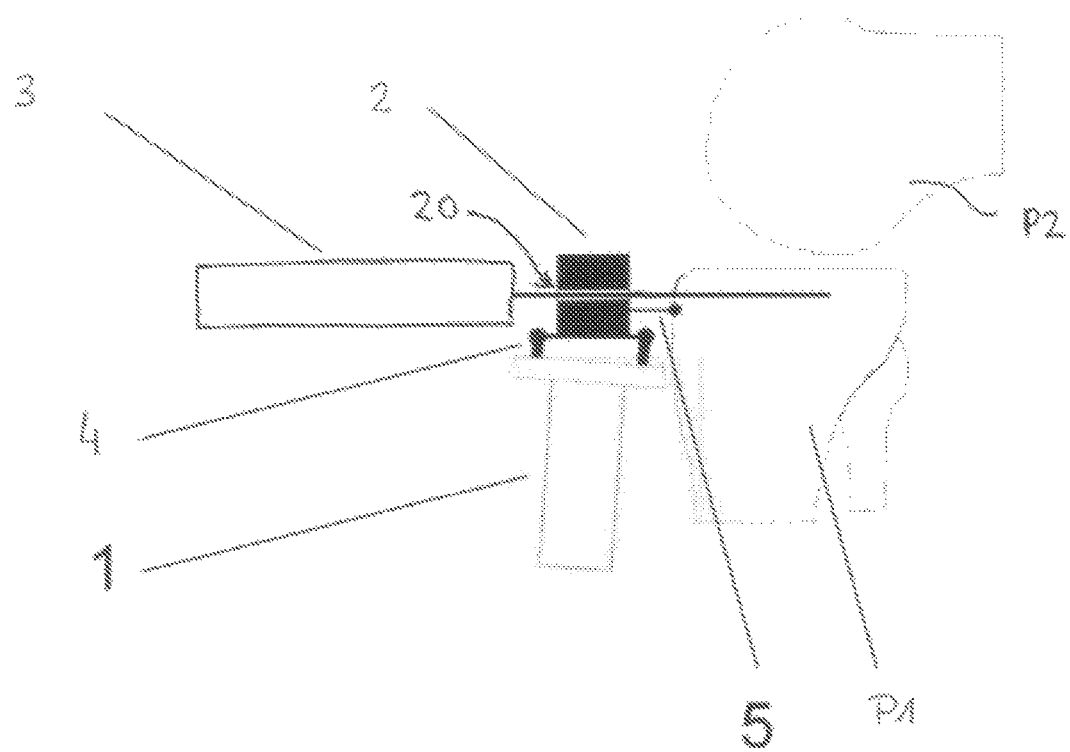

FIGS. 3A to 3C illustrate examples of embodiments of the handheld device.

FIGS. 3A to 3C are intended to provide a general description of the handheld device, although the invention may be implemented according to various embodiments.

A description of some specific embodiments—related to specific surgical applications—will be described below.

Base

The handheld device comprises a base 1, which is intended to be hand-held by the surgeon.

To this end, a specific handle may be mounted on the base, or the base may itself be designed so as to provide an ergonomic shape.

Tool/End-Effector

The handheld device further comprises an end-effector 2 on which a surgical tool 3 dedicated to the intended treatment can be mounted (see FIGS. 3A-3B).

According to an embodiment, the tool 3 may be factory-mounted on the end-effector 2; otherwise, the end-effector may comprise an attachment system (e.g. a clip-on mechanism) to secure a tool which may be a conventional tool provided separately. This embodiment has the advantage of being easily compatible with a sterile drape used to cover the actuation unit and the end-effector.

As a result, the tool 3 may or may not be part of the device.

According to another embodiment (see FIG. 3C), the end-effector supports a guide 20 for the tool dedicated to the intended treatment.

When the tool is a saw, the tool guide is a cutting guide that defines a cutting plane (2D volume to be removed).

When the tool is a burr, the tool guide is a drilling guide that defines a milling line (1D volume to be removed).

The tool guide 20 may be factory-mounted on the end-effector 2; otherwise, the end-effector may comprise an attachment system (e.g. a clip-in mechanism) to secure a conventional guide.

The tool guide may be fixed or movable (e.g. slidable and/or rotatable) with respect to the end-effector.

Actuation Unit

As shown on FIGS. 3A-3C, the end-effector 2 is connected to the base 1 by an actuation unit 4, in order to move the tool 3 or, if appropriate, the tool guide 20, with respect to the handheld base for treating the planned volume.

The actuation unit has a given number of degrees of freedom depending on the application.

The actuation unit 4 comprises motors, gears (optional) and sensors connected together to form a kinematic structure.

As it will be explained in more detail below, the actuation unit 4 is controlled by the control unit 300.

According to one embodiment, the tool 3 can be a spherical burr or shaver and the volume to be removed is modeled as the union of spheres having the same diameter as the burr or shaver.

In such case, the actuation unit 4 is designed so as to have three degrees of freedom (in addition to one degree of freedom to activate the rotation of the burr).

A further optimization may comprise five degrees of freedom to adjust the orientation of the tool's cutting edges relative to the part to be treated.

In another embodiment, the tool can be a cylindrical burr or shaver and the volume to be removed is modeled as one possible union of cylindrical segments having the same shape as the burr or shaver.

In such case, the actuation unit is designed so as to have five degrees of freedom.

The volume to be removed can also be represented by voxels, triangulated mesh data, coordinates of a plane (for sawing mode); points, directions and depth (for bore holes). And the actuation unit design will be adapted to the type of volume to be treated.

It is possible to make the actuation unit a sterile component, to be sterilized before each intervention. But, in a preferred embodiment, the actuation unit and its cables are covered by a single-use transparent plastic sterile drape. Additional components of the system can be also protected under the sterile drape. But the tool itself is sterile, like any conventional tool. Typically, it is sterilized before each intervention using autoclave. Different types of mechanical adaptors between the sterile drape and the tool can be provided. Such adaptor does not require a very precise reproducible fixation if the tool contains a tracking element, which facilitates the design and the use of the global system.

Support Unit

The handheld device further comprises a support unit 5 which is connected either to the base 1 (see FIGS. 3A-3B) or to the end-effector 2 (see FIG. 3C).

Said support unit 5 comprises at least one element intended to make contact with the part to be treated or an area of the patient's body adjacent to the part to be treated so as to provide a partial mechanical link between the base 1 (or the end-effector 2 as shown in FIG. 3C) and the part to be treated. The user is trained to always apply pressure to the support unit to ensure sufficient contact with the part to be treated.

The support unit 5 is usually a sterile component. The connection between the support function and the base or end-effector can be established on the sterile drape if the actuation unit with its base and end-effector are covered with a sterile drape. Or it is established directly if the base or end-effector is sterile.

The support unit 5 is a critical element of the handheld device that acts as a stabilizer.

Said support unit may be rigid, damped (e.g. spring-loaded) and/or provide adjustable damping properties.

The contact between the support unit 5 and the body part may be made of one or several points or of at least one surface.

In the embodiment shown in FIGS. 3A and 3C, the support unit 5 comprises a rigid pin in contact with the part P1 to be treated.

According to an alternative embodiment (see FIG. 3B), the support unit 5 comprises a damped pin which is in contact with a part P2 of the patient's body adjacent to the part P1 to be treated.

According to an embodiment, when the end-effector 2 supports a tool guide 20, the support unit 5 may comprise the tool guide 20 itself (see FIG. 3C).

In each case, due to the fact that the support unit 5 makes either direct contact with the part P1 to be treated itself or indirect contact via a region P2 of the patient's body adjacent to part P1, the support unit 5 has the effect of a partial mechanical link that limits the movements of the user when operating the device—and, in advantageous embodiments, also damps movements of the user, vibrations of the cutting tool and reaction forces caused by movements of the actuation unit.

In addition, as the support unit only provides a partial mechanical link, it does not require any invasive action.

Without this limitation effect, all user movements with respect to the part to be treated would have to be compensated in real time by the actuation unit, which is extremely difficult to achieve with existing robotic technologies.

Micro or macro motions of the user with respect to the part to be treated, including slow and fast motions, must be compensated within a tolerance range that defines the device's precision.

Typically, for bone surgery applications, motions in the range of a few tenths of a millimeter need to be compensated to obtain sufficient precision; such compensation requires ultrafast motion detection and measurement, as well as calculation of the compensation motion to be applied and execution of desired compensation motion. Non-compensated motions result in bumpy or irregular surfaces.

For dental applications, the required precision is even higher, typically in the range of a few hundredths of a millimeter.

Sensors, computers, motors, controllers, low inertia mechanisms able to achieve the performance described above do not exist or would be extremely costly to develop and manufacture.

By considerably limiting—and preferably damping—motions, the support unit makes it possible to use existing robotic technologies to obtain the required precision.

The partial mechanical link is also important when the part to be treated is being treated.

The support unit enables a short closed force loop of the forces exerted during treatment via the device back to the part where the support unit is on.

Only a small quantity of the forces exerted during treatment needs to be compensated by the user, the result of which is higher accuracy.

Depending on the type of support unit, parts of the forces exerted will be damped by the closed force loop.

For example when using one sharp pin as support, the forces in two directions can be damped parallel to the surface where the pin is located.

For example, the partial mechanical link may be achieved by one or more sharp-tipped pins able to prick the bone when the device is pressed on the bone by the surgeon.

Figure 3D:
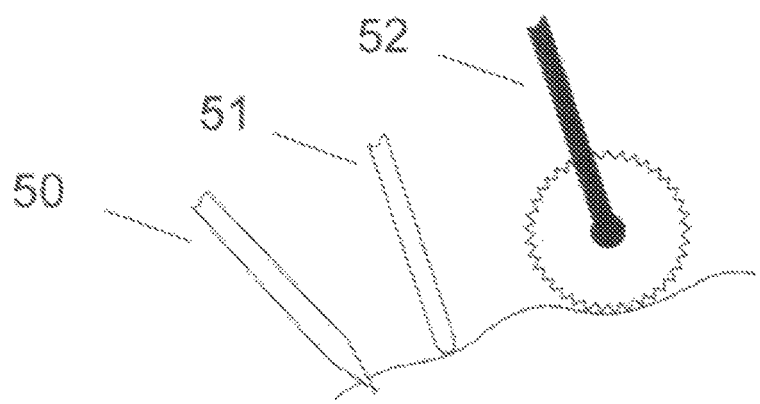

Such a sharp pin is referenced to as 50 in FIG. 3D.

Such a sharp pin 50 creates a partial link consisting of three degrees of freedom.

When two sharp pins are used, only one degree of freedom is allowed about the axis passing through both pin tips.

The partial mechanical link may also be achieved by one or more pins having a rounded tip which may be pressed by the user onto the bone when using the device (see reference 51 in FIG. 3D).

The tip of the pin may also have a silicone disc (not shown) attached to it providing a damping effect.

According to another embodiment, the support unit may comprise at least one wheel provided with several sharp teeth, such a wheel being able to slide on the bone in at least one direction and optionally allowing a rotation about the wheel axis (see reference 52 in FIG. 3D).

According to another embodiment, the support unit comprises an attachment device having a surface attached to or at least in contact with a part of the patient's body so as to fit the shape of said part and at least one pin connecting said attachment device to the base or the end effector of the handheld device. The attachment device advantageously prevents the pin end from sliding with respect to the patient's body. The connection between the pin and the attachment device is preferably reversible and can make use of any type of connection (mechanical, magnetic, etc.). For example, the connection may include hook-and-loop fasteners such as Velcro®, magnetic fasteners (e.g. the attachment device comprising a metal and the pin end comprising a magnet), or a mechanical articulation.

Figure 3E:
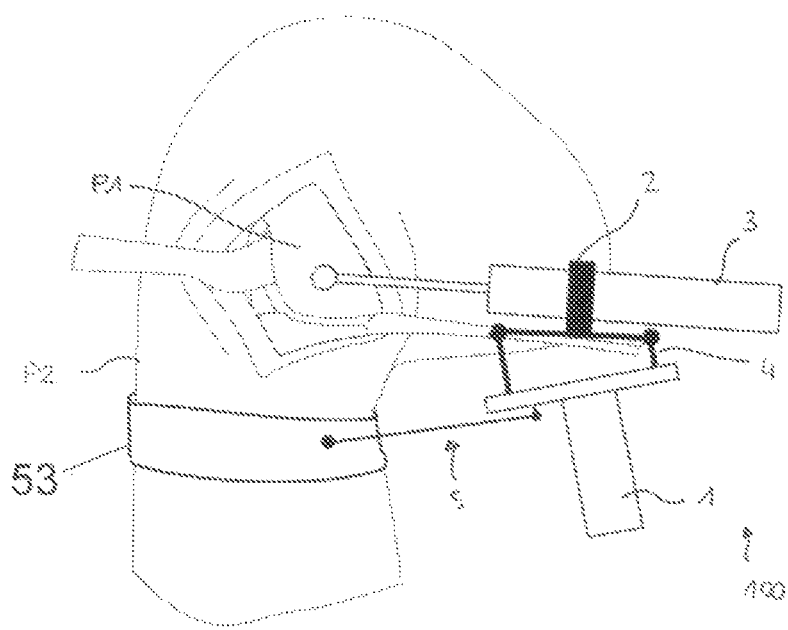

As shown in FIG. 3E, the support unit 5 may also comprise a tourniquet 53 to which the support pin end is connected and that acts as a strap compressing the soft tissues around the bone, thus creating a non-rigid link that is standard and well accepted for other purposes. In the present text, the term tourniquet is used for defining a strap attached around the soft tissues (skin) with or without the function of stopping blood. The connection between pin end and tourniquet bears shear forces and thus prevents the pin from sliding on the soft tissue. As mentioned above, the connection mechanism may be designed as hook-and-loop fastener or a magnetic fastener.

Figure 3F:
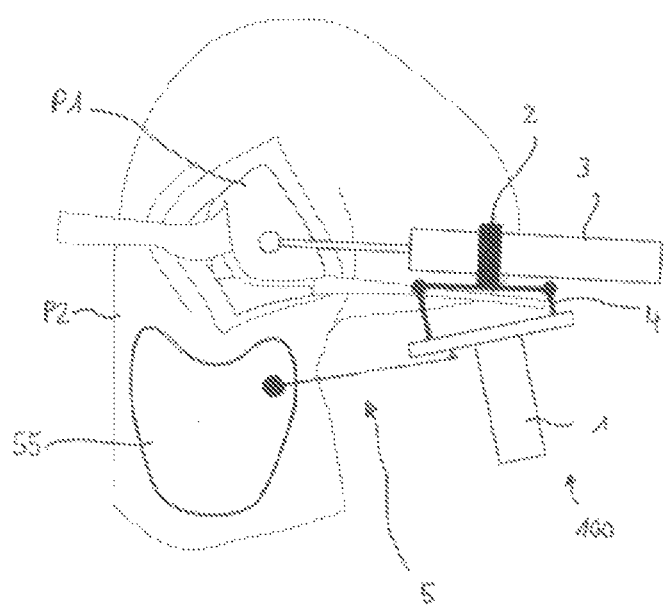

An alternative embodiment may comprise an adhesive patch 55 instead of the tourniquet, which is attached to the skin of the patient and connected to the pin end (FIG. 3F). The external surface of the patch advantageously prevents sliding of the pin end.

Alternatively, the attachment device may be formed by applying a moldable material onto a part of the patient's body. For example, pastes used in dentistry are able to be molded and to harden quickly, possibly assisted by a heater without any damage to the patient, by using a thermoforming process. The molded device thus forms a template that fits the shape of the patient's body.

Figure 3G:
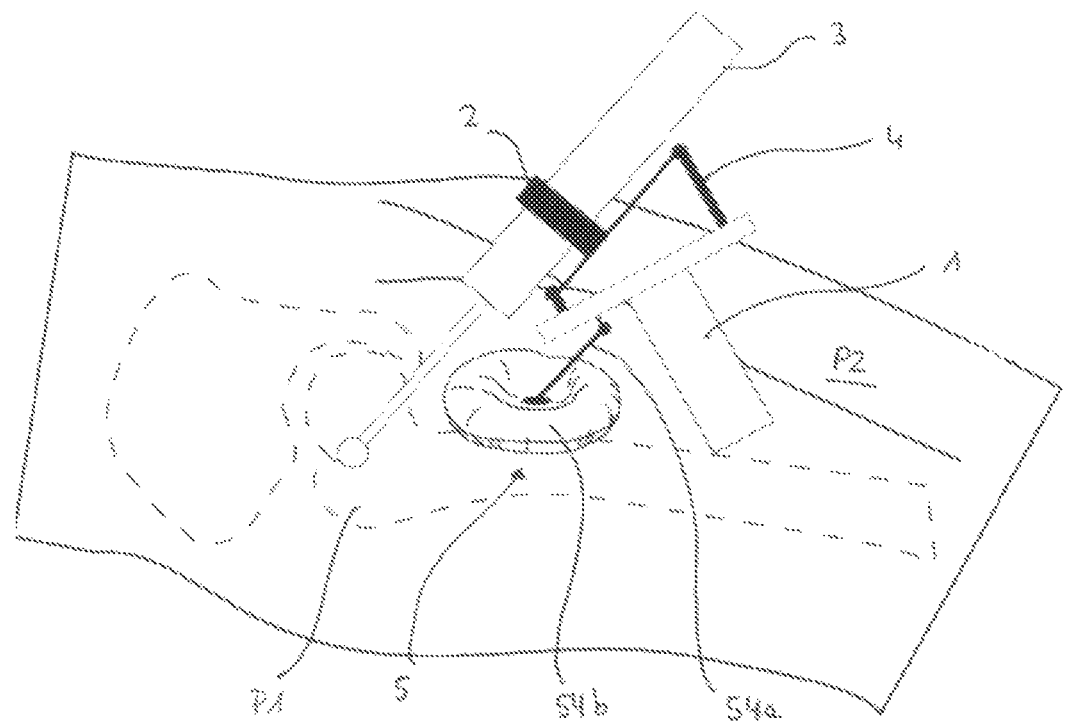

According to another embodiment, illustrated in FIG. 3G, the support unit 5 may comprise a pin 54a, one end of which is connected to the base 1 and the other end of which is connected to a deformable cushion 54b (similar to a sand sack), which provides a damped support function.

Such a cushion is intended to be placed on the patient's skin, in a vicinity of the entry port of the tool.

Optionally, such a deformable cushion 54b may be fixed by vacuum in order to provide more rigid support.

In a similar embodiment, illustrated in FIG. 9A/9B, the end of the pin 54a may be disk-shaped 54c, made of plastic for example, with a surface intended to be in contact with the patient's body. Such a pin end may be coated with a flexible type of material (such as silicone or foam) for better adhesion to the patient's skin. The pin is generally made of metal, e.g. steel.

The connection between the pin 54a and the cushion 54b or the disk 54c may take the form of a ball and socket joint (not shown).

The ball is advantageously at the end of the pin 54a and is made of metal, whereas the socket is integrated into the cushion 54b or the disk 54c and is made of plastic.

The ball and socket joint can thus be easily connected and disconnected by elastic deformation of the socket.

Consequently, the user may first install the cushion 54b or the disk 54c in a suitable place on the patient's body, then take the handheld device 100 and connect the pin 54a to the cushion 54b or the disk 54c via the ball and socket joint to assemble the support unit 5.

Conversely, when the user stops using the handheld device 100, the user can disconnect the pin 54a from the cushion 54b or the disk 54c and later move or remove the cushion 54b or the disk 54c from the patient's body.

The support unit 5 may advantageously provide damping such that said partial mechanical link created between the base and the part to be treated is able to absorb reaction forces exerted by the treated part onto the tool.

Said damping characteristics may be provided by a spring-loaded element or by a pneumatic or hydraulic damper.

Advantageously, the damping characteristics of the support unit may be adjustable.

Damping presents the advantage of higher accuracy when the user does not have to compensate the reaction forces.

Figure 3H:
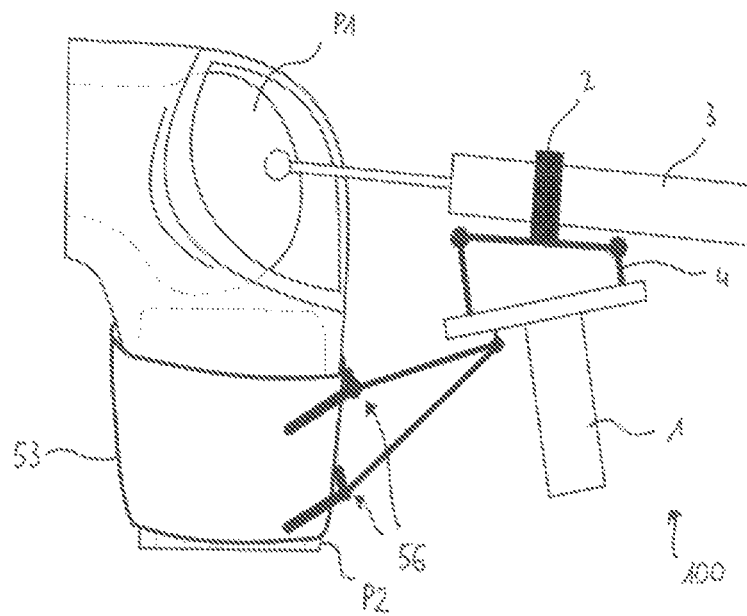
Figures 3I, 3J:
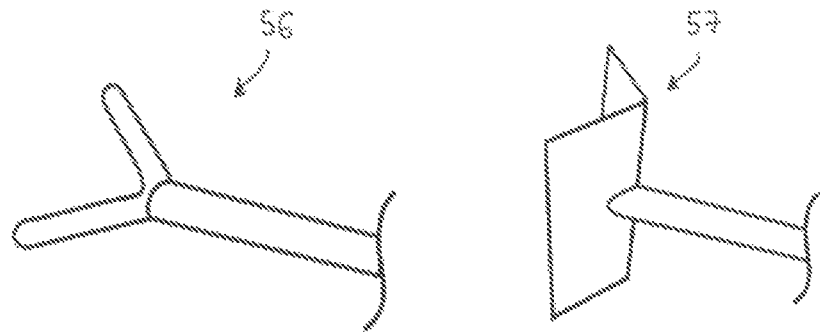

In another embodiment, illustrated in FIG. 3I, the support unit comprises at least one pin 56 having a V shaped end with circular cross sections, providing one not stabilized degree of freedom between base and patient.

This degree of freedom may be blocked by using two of such these pins 56 (FIG. 3H) or by using a pin 57 having an end formed like an angle bracket (FIG. 3J). The V shape of the pin end(s) provides a template for alignment with the tibial crest line and thus a possibility for coarse positioning of support unit and handheld device.

This embodiment is particularly advantageous in UKA because the support unit provides a limited number of positions that make it possible to reach both areas to be milled on the tibia and on the femur, in a quick and intuitive manner.

More generally, the support unit can be designed to have a predefined shape that fits the external surface of a patient anatomy such that the robot base will be positioned immediately in an area wherein the corresponding robot workspace will match the volume of the part to be treated.

Optionally, as shown in FIG. 3H, a combination with the above-mentioned tourniquet 53 or adhesive patch 55 with Velcro® or magnetic fastening mechanism is possible in order to prevent sliding of the V shaped pin end(s) with respect to the tibial crest.

Figure 3K:
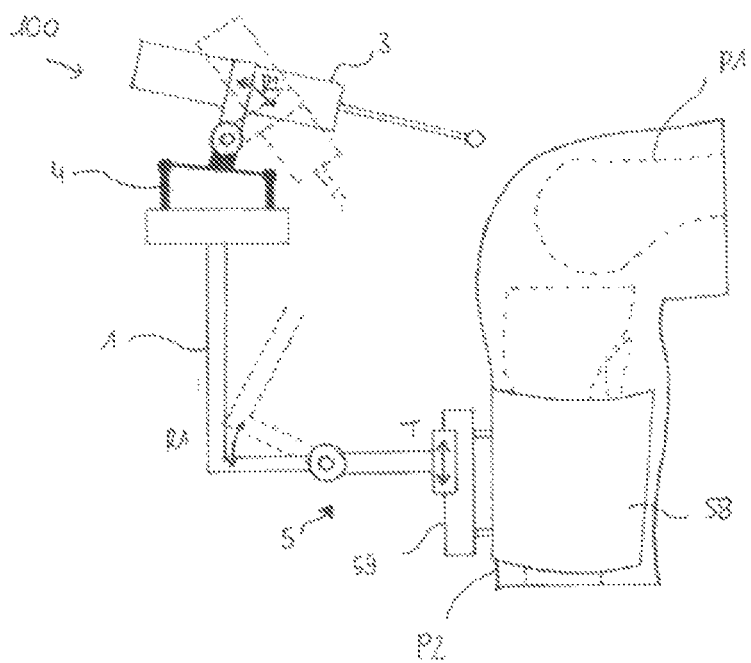

According to an embodiment illustrated in FIG. 3K, the support unit 5 comprises an attachment device 58 such as a tourniquet, an adhesive patch or a template as described above, attached to a part of the patient's body (here, P2 designates the tibial crest). A mounting element 59 is fixed to the attachment device 58. The base of the handheld device is coupled to the attachment device by a connecting member in sliding engagement with the mounting element 59 (translation movement T along the tibial crest). The connecting member advantageously comprises a joint that allows rotation R1 of the base. If the end effector or the tool is also allowed to pivot with respect to the actuation unit 4 (rotation R2), the tool is able to reach all or almost all necessary different parts of the patient's body without moving the base of the handheld device.

Figure 3L:
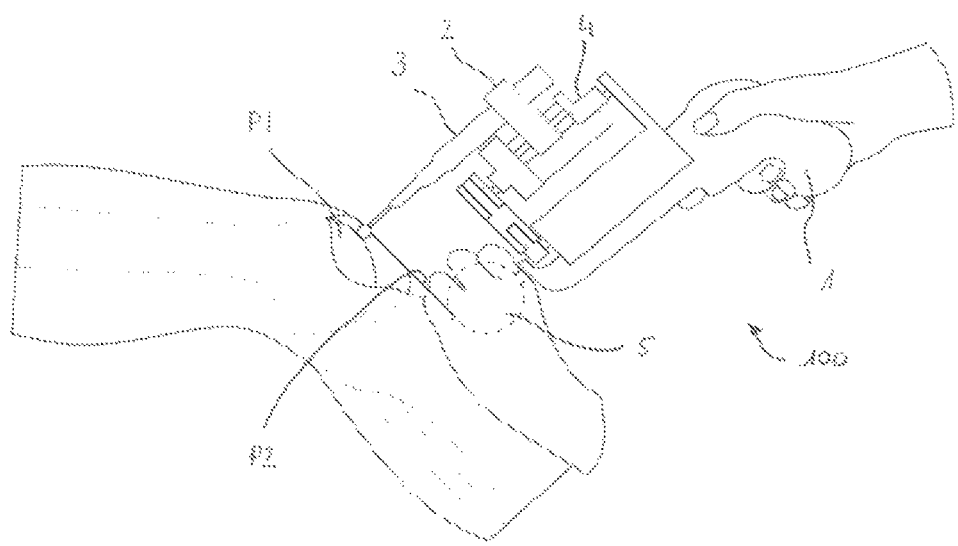

According to an embodiment illustrated in FIG. 3L, the support unit 5 may be designed as a second hand grip for the user (in addition to the part of the base that is normally held by the user). For example, in FIG. 3K, this hand grip is designed as a ball that can be held in the second user's hand, the first hand holding the base. Then the partial mechanical link between the patient and the device is provided by the second hand of the user that leans on the patient's body, which is able to stabilize and damp relative movements.

According to an embodiment (not illustrated), the support unit may also comprise at least one sensor for detecting a force exerted by the user onto the partial mechanical link; hence, the control unit is able to check whether said force is greater than a threshold such that the support unit has a minimal damping parameter. This ensures that for example the sharp pins may not slip on the bone.

If not, the control unit may emit an alert to the user or automatically stop the device.

Depending on the application, the above-described embodiments of the support unit may be combined to provide a suitable partial mechanical link between the handheld device and the patient's body.

The support unit 5 is preferably designed so as to be disconnectable from the handheld device 100, in particular for sterilization and/or replacement of the element providing the support function.

For example, but non-limitatively, ball and socket joints may be used to connect and disconnect the support unit to the base or to the end-effector easily.

If the support unit 5 is connected to the base 1, it only generates a global constraint that will prevent the user from placing the tool 3 anywhere in a large space, but it will not generate any limitation to reach any volume or target in its vicinity.

The actuation unit 4 will continue to act and compensate for the relative motions between the base 1 and the part 100 to be treated, whilst continuously optimizing the milling path.

The support unit 5 is intended to help solve the complex control and dynamics of the system but not to add a geometric constraint in a local neighborhood.

At some point, the support unit 5 may generate a global constraint that requires the user to move the base and/or the support unit contact areas.

Tracking Unit

The system also comprises a tracking unit 200 configured to determine in real time the pose of at least one of the tool 3, the end-effector 2 and the base 1 with respect to the part 100 to be treated.

The pose of the tool 3 relative to the end-effector 2 may be either known and mechanically determined, or not.

Knowledge of the tool pose relative to the end-effector may be useful in view of redundancy calculation based on kinematics.

The tracking unit may typically comprise a tracking system, which is known per se.

Tracking systems commonly used in computer-assisted surgery use a variety of different technologies (passive optical, active optical, electromagnetic, inertia with gyroscopic measurements, ultrasonic, etc.) that can be used individually or in combination.

The tracking unit measures the pose of a first object equipped with a tracker with respect to another reference second object also equipped with a tracker.

In some cases, the reference second object is the tracking unit itself and only one tracker is necessary on the first object.

A tracker can be an emitter or a sensor (also called receiver).

In all cases, the tracking unit provides a transform matrix between the pose of the part to be treated and the pose of the tool and/or the device.

The typical frequency of the tracking unit is in the range of 50 Hz to 1000 Hz or even more.

In the appended drawings, emitters 210 are represented by a triangle whereas sensors 220 are represented by a square.

Emitters and sensors can be redundant to increase accuracy of pose measures.

In the example of an electromagnetic tracking system with several possible configurations for emitters and sensors, we consider that the measure obtained between an emitter attached to a first object and a sensor attached to a second object fully determines the relative pose of the first object with respect to the second object. Said pose is usually represented by a matrix representing a 3D rotation and a vector representing a 3D translation.

If a sensor is attached to a third object, elementary combination of matrices determines the relative pose of the third object with respect to the second object (that is to say between two sensors).

As shown in FIGS. 4A-4E, various arrangements of emitter(s) and sensor(s) are possible.

Preferably, the distance between the sensor and the emitter is minimized so as to minimize the possibility of distortions induced by surrounding metallic objects.

According to a preferred embodiment, the emitter is mounted on the device itself, more precisely on the base or on the end-effector.

Only one sensor mounted on the part to be treated may be sufficient.

This has the advantage of reducing the number of necessary coordinate system transformations and thereby reducing error occurrence and increasing accuracy.

In some cases, e.g. when the tool is a shaver or a small diameter burr, not rigid enough to allow tool tip pose determination based on the pose of the end-effector, an additional sensor may be mounted on (or close to) the tool tip.

Figures 4A, 4B:
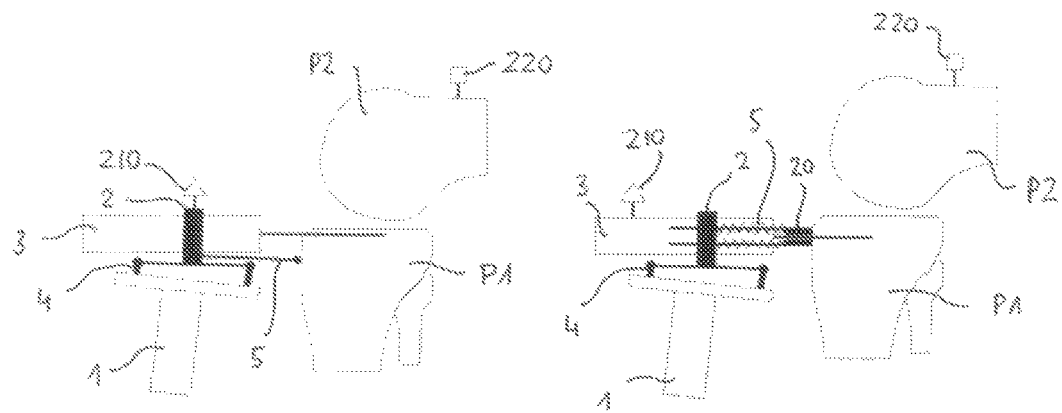
FIGS. 4A to 4D show devices with different implementations of the tracking unit.

In FIG. 4A, the tracking unit comprises an emitter 210 located on the end-effector 2 and a sensor 220 located on the patient's body (here, on a part P2 adjacent to the part P1 to be treated).

In FIG. 4B, the tracking unit comprises an emitter 210 located on the tool 3 and a sensor 220 located on the patient's body (on a part P2 adjacent to the part P1 to be treated).

In this particular embodiment, the support unit 5 and the tool guide 20 are connected to the end-effector 2 and are spring-loaded, so that under a pushing action the tool 3 (here, a sawblade) can slip out of the guide 20.

Figures 4C, 4D:
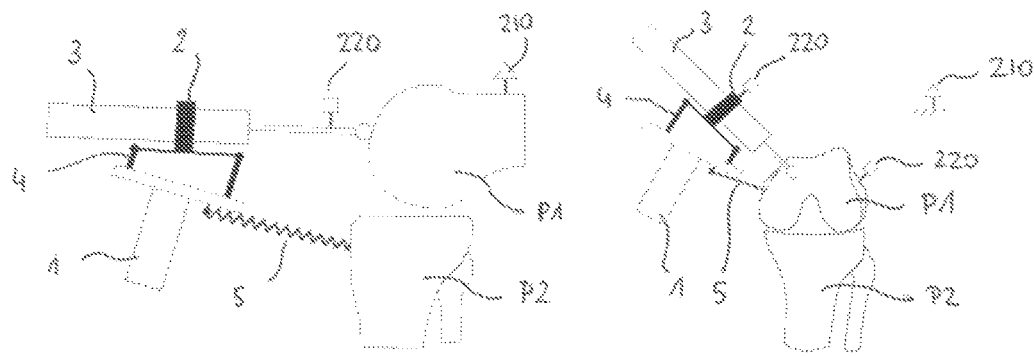

In FIG. 4C, the tracking unit comprises a sensor 220 located on the tool tip and the emitter 210 on the part P1 to be treated.

In FIG. 4D, the tracking unit comprises an emitter 210 located in the operating room and two sensors 220: one on the end-effector 2 and the other one on the part P1 to be treated.

Figure 4E:
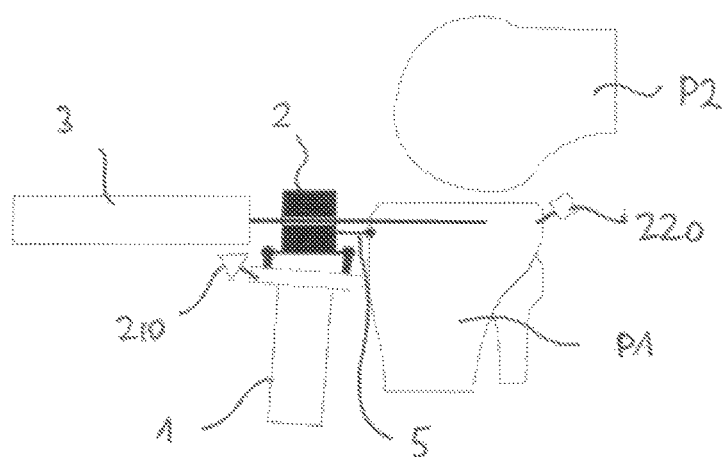

In FIG. 4E, the tracking unit comprises an emitter 210 located on the base 1 of the device and a sensor 220 located on the patient's body.

In addition, it should be noted that knowledge of the actuation unit kinematics and end-effector geometry may also be used to determine the transform matrix between the base pose and the tool pose. If an emitter or sensor is attached to the base, and a sensor is attached to the tool, one obtains redundant measurements that are used for safety and optimization purposes.

Of course, the above-described embodiments are only examples and a skilled person may arrange the sensor(s) and emitter(s) in a different way, or combine some of these embodiments, without departing from the scope of the invention.

User Interface

As mentioned previously, a user interface is defined so as to show the user a safe device position.

In most cases, intrinsic safety is achieved when the working space of the tool is smaller than the volume to be treated. This also results in small device dimensions and thus a lightweight and compact handheld device.

The user interface may provide information to the user to guide him or her to reposition the device continuously in an optimal pose.

Said user interface may be haptic, visual and/or acoustic.

According to an embodiment, the user interface 400 may comprise a screen 410 connected to the control unit, e.g. the screen shown on FIG. 1.

Figure 5A:
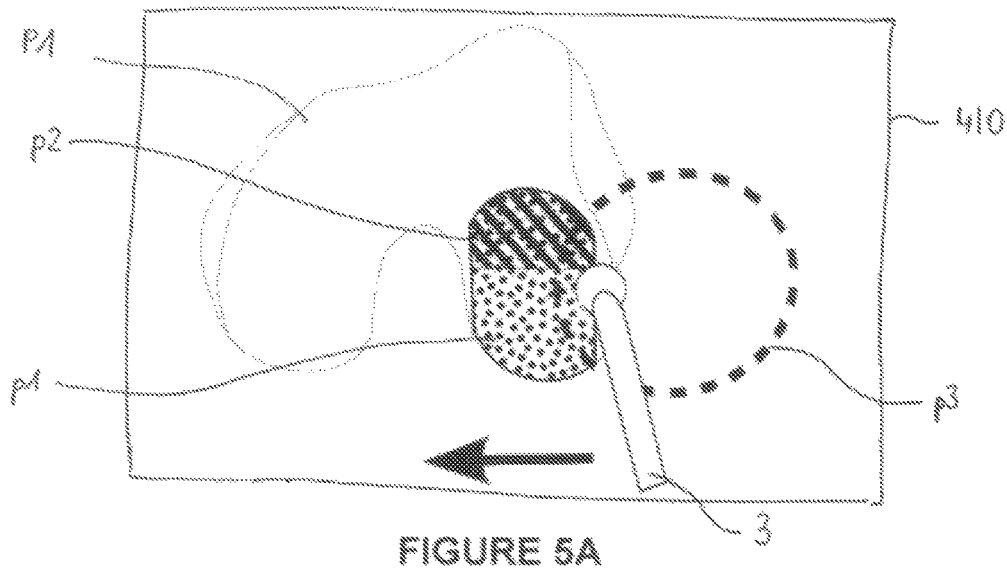
FIGS. 5A to 5C show different embodiments of the user interface.

As shown in FIG. 5A, said screen 410 displays, e.g. in the form of an arrow, the adjustments necessary to maintain continuous treatment of the whole volume.

This adjustment information may also be visualized on an endoscopic image (e.g. in FAI treatment).

During the use of the device the control system checks in real time if the volume to be treated can be processed safely. If the robot base is moved such that the border of the workspace comes closer to the volume to be treated, meaning that there is not much space for error compensation, then the information provided to the user may change, e.g. the arrow changes its color or an acoustical feedback is produced.

According to another embodiment (see FIG. 5B), the user interface comprises optical indicators 420 such as LEDs supported by a supporting plate 421 that is fixed to the device 100.

Said indicators 420 are connected to the control unit 300 and placed so as to show the user in which direction and/or orientation the device has to be moved to ensure non-interrupting treatment.

The LEDs can be multi-colored or blink at different frequencies to indicate how much and/or how soon correction in the pointed direction is necessary.

Since the indicators 420 are arranged on the device 100 itself, the surgeon receives this pose information in situ, which is very convenient for him or her.

Another way of providing information to the user is an optical projection of repositioning information directly on the patient's skin or bone.

Figures 5B, 5C:
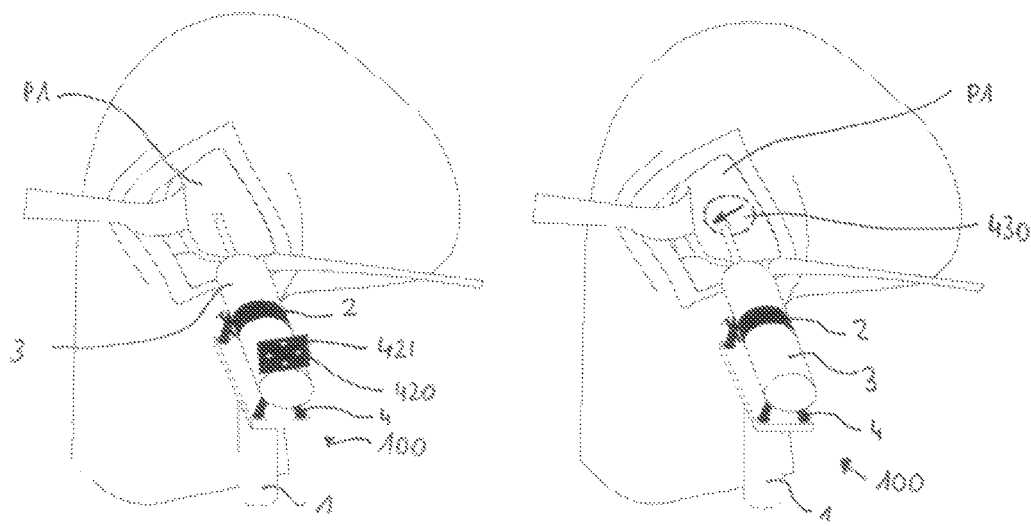

For example, as shown on FIG. 5C, the information may take the form of an arrow 430 projected by a laser pointer (not shown) arranged on the device 100 and controlled by the control unit 300.

Control Unit

The system further comprises a control unit which is intended to control the tool path in an optimal way in order to treat the planned volume.

Operation of the control unit will be described in more detail below.

Figure 6:
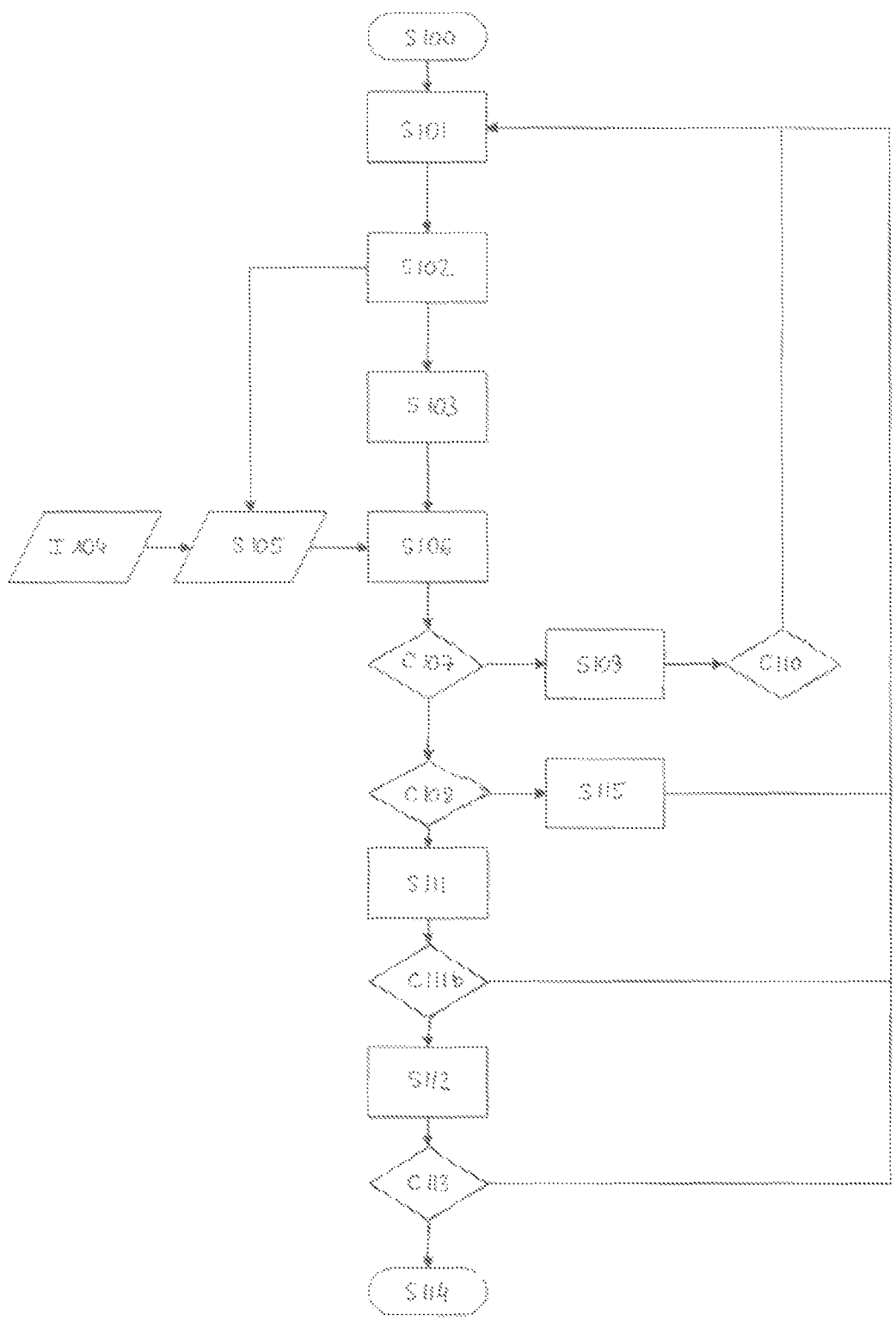
FIG. 6 is a flow chart representing a way of implementing a system according to the invention.

FIG. 6 is a synoptic drawing showing a possible operation of the system. The method described here is suitable for UKA and treatment of FAI. However, a skilled person will be able to adapt it for other surgical procedures.

The planning phase is carried out before system operation.

In step S100, the user starts operating the device described above.

In step S101, the pose of the tool tip with respect to the part to be treated is measured by the tracking unit.

In step S102, the control unit updates the remaining volume of the part to be treated which at the beginning of the process is the entire planned volume to be removed.

In step S103, the control unit determines the pose of the end-effector with respect to the base.

Based on the planned volume to be treated (input 1104), the control unit determines the remaining volume to be treated (step S105) and, based on the pose of the end-effector with respect to the base, determines the part of said volume that can be treated safely (step S106).

Safely means here, that at any position of the safely removable volume, the device is able to compensate for errors caused by movements induced by the user. This could be that the device is able to move the tool for a certain defined amount of millimeters with a determined speed or within a determined time or rotate it by a certain defined amount of degrees. To be able to do this, the dynamic behavior of the end-effector at each pose with the working volume has to be known.

In step C107, the control unit checks whether the tool tip is inside the planned volume or not.

If not, the control unit stops the tool and device immediately and generates a message for the user (step S109).

Advantageously, the position data may be previously filtered so as to avoid stopping the device if outlier values are obtained.

If the user acknowledges this alert (step C110) then the method begins again from step 101.

To that end, the user has to reposition the device as may be indicated by the user interface (preferred embodiments of such a user interface are described above).

If the tool tip is inside the planned volume, the control unit checks whether the safely treatable part of the volume is above a given threshold (step C108).

The threshold may be implemented in different ways. One could be that the size of the remaining volume is smaller than a defined size. Another implementation could be that the distance to the border of the safely removable volume is smaller than a defined value.

If not, the control unit 300 indicates, via the user interface 400, that the user should reposition the device in a calculated direction (step 115). This repositioning may include changing the position of the support unit, or may be made without changing the position of the support unit (e.g. by moving the base along the free degrees of freedom of the support unit). For example, the user interface may indicate to pivot the base of the device around a fixed support tip, in a given direction and for a given amount, until it has reached a pose that will allow reaching a new sub-volume of the part to be treated, said sub-volume having a size above a predefined threshold. Then the method iterates again from step 101.

If the safely treatable part of the volume is above said given threshold, the control unit calculates an optimized path of the tool tip in the coordinate system of the device (step 111). The optimized path may comprise not only poses at specific time steps but may also include tool parameters, such as changing the rotation speed of the milling device depending on the tool pose. In other words, the optimized path may contain poses according to six degrees of freedom and processing parameters at each time step.

If the user enables the process via hand or foot switch (step C111*b*), then the control unit adjusts the actuation unit so as to move the end-effector according to said computed path (step 112). As the path is defined in coordinates of the sensor on the part to be treated, and the control unit minimizes the distance between the tool tip and the current pose of the computed path at each time step, the device will follow the path, independently of movement that the user applies to the device.

The control unit checks whether the remaining volume to be treated is below a given threshold (step C113).

Said given threshold may be defined by the user as a limit equating to a satisfactory treated volume, even if the treated volume is not exactly identical to the planned volume.

In the affirmative, the method ends (step S114).

If not, the method iterates again from step S101.

The iteration may be carried out at high frequency (e.g. 1000 kHz).

In the case of TKA, the method differs slightly from the method described above.

For this intervention, there are two possibilities:
first, the tool (a sawblade) is distinct from the device and is handled in a first hand of the user (or an assistant) whereas the device is handled in a second hand (of the user or of an assistant) (see FIG. 4E for example),
second, the tool is part of the device and, by pushing the device onto the bone, the tool slides out of the guide into the bone (as shown in FIG. 4B).

In step S101, the pose of the end-effector or the support unit with respect to the bone is determined.

In step C113, it is the user who decides whether the planned 2D volume has been removed.

Depending on the application, it is possible that the base requires re-positioning several times, typically three or four, but sometimes as many as one hundred. However, when a large number of re-positioning actions are necessary, discrete positions of the base are not necessarily required. Instead the base may move continuously and slowly to cover the necessary complete working space. For complex shapes to be treated, the user may be asked to move the base continuously for a given position of the support unit, then move the support unit to another fixed location, and then move the base continuously in that vicinity, and to repeat this process until the complete volume has been treated.

The repositioning of the base or of the support unit may be guided by the user interface so as to reach a new position from which without a new change maximal volume can be removed. This is to minimize the number of necessary repositioning steps.

As mentioned above, the optimized path may comprise poses and processing parameters (e.g. the tool speed) at each time step.

Holding Arm

Figure 10:
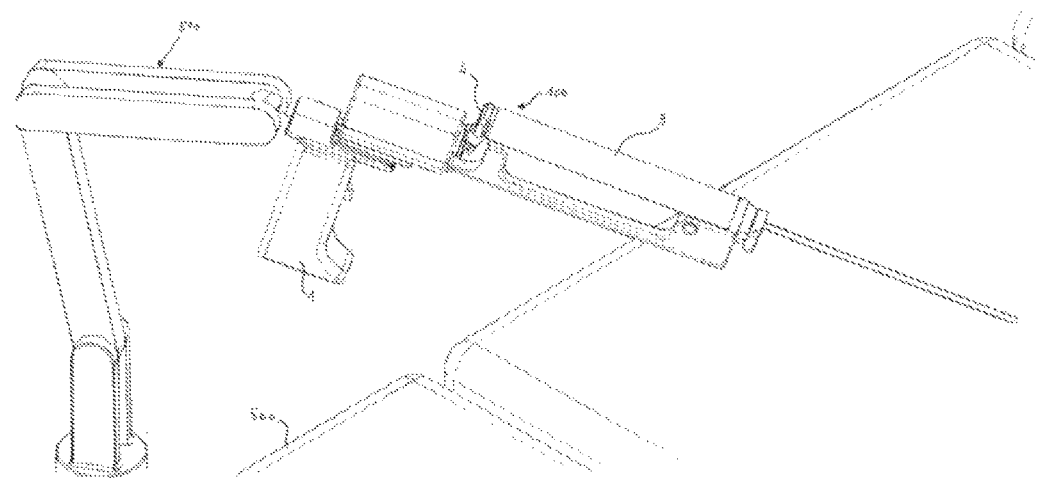
FIG. 10 shows a further embodiment wherein the handheld device is supported by a holding arm.

According to one embodiment, illustrated in FIG. 10, handling of the handheld device 100 may be assisted by a holding arm 510 that supports the base 1 of the handheld device 100 and that is connected to a mechanical support.

The holding arm 510 is articulated with several degrees of freedom and a switch is used to brake or freeze its position (pneumatic arms, hydraulic arms, mechanical arms, arms with brakes, etc.). In addition, a holding arm may have a mechanism to compensate for the weight of the handheld device that it carries (by using passive or active counterweights for example).

In this case the holding arm is considered to be another possible embodiment of the support unit previously described.

Another variation is to use a local support element in addition to the holding arm, similar to the embodiments of the support unit previously described.

The holding arm 510 is articulated so as to allow the user to position the handheld device 100 in a desired position.

The holding arm 510 allows compensation for the weight of the handheld device 100 and minimizes user tiredness, especially if the surgical procedure takes a long time.

Preferably, said mechanical support is in contact with the patient's body.

The mechanical support also contributes to create a partial mechanical link between the part to be treated and the handheld device.

The mechanical support is preferably the operating table 500 or a support element which is commonly used to position and hold the patient (e.g. leg holder, pelvis holder, operating table post, etc.).

Additional local support may be achieved by integrating a support element on the end-effector 2 or the base 1 as described above to have a smaller force chain to compensate, with fewer vibrations. This embodiment is particularly useful if the mechanical support of the holding arm is simply a mobile cart or is ceiling-mounted.

Holding Cable

Figure 11:
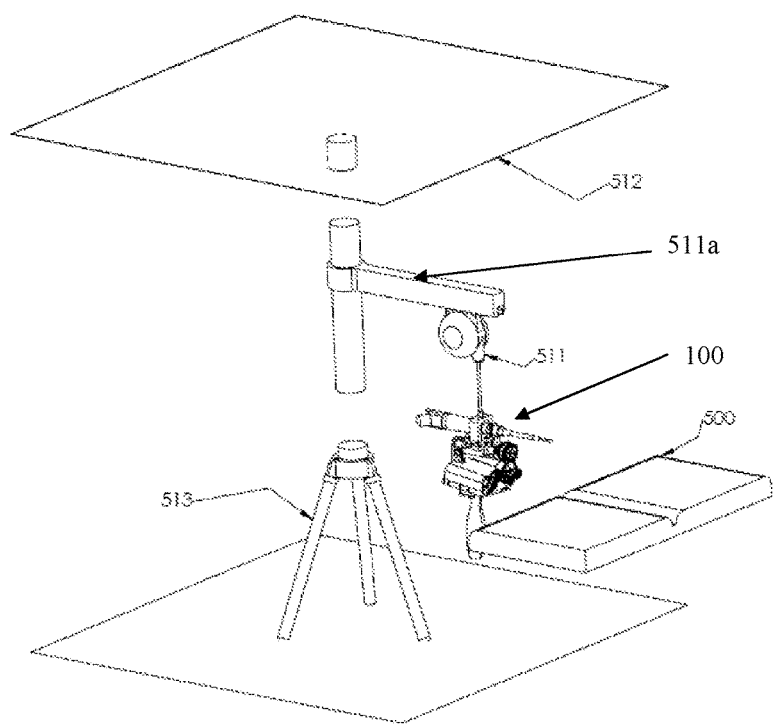
FIG. 11 shows a further embodiment wherein the handheld device is supported by a cable extending from a spring pulley.

According to a further embodiment, illustrated in FIG. 11, handling of the handheld device 100 may be assisted by a cable extending from a spring pulley 511 that supports the base 1 of the handheld device 100 and that is connected to a mechanical support 511a.

The holding cable 511 allows all degrees of freedom of the handheld device at all the time of the use.

In addition, the holding cable may have a mechanism to compensate for the weight of the handheld device that it carries (by a weight adjusted for the return spring to wing the cable, for example) in order to minimize user tiredness, especially if the surgical procedure takes a long time. In that way, when the handheld device 100 is released, it remains in its position or back up slightly.

The mechanical support 511a can be either supported by the ceiling 512 of the room, by a fixed or mobile cart 513 resting on the floor, or by the operating table.

The partial mechanical link is provided by a support unit (not shown) on the end-effector 2 or the base 1 as described above.

Example of Application No 1—Uni Knee Arthroplasty (UKA)

In UKA, the tool is used to prepare tibial and femoral bone for implant fixation at a planned position and orientation. The volume to be removed coincides with the negative shape of the implant when it is in its final position.

The used milling strategy could also be used for all other applications where a cavity has to be removed or the bone surface has to be reshaped as when using patient specific implants.

In this respect, a (3D) bone volume both at the femoral and at the tibial side has to be removed for the insertion of the implant components.

To that end, the tools used are typically mills and shavers.

Figure 7A:
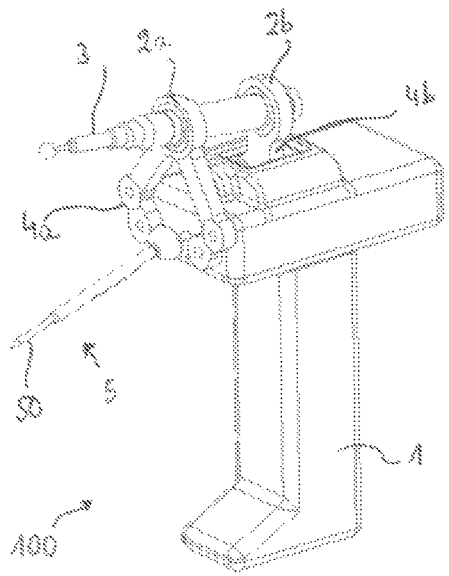
FIGS. 7A and 7B show an embodiment of a handheld device suited for uni knee arthroplasty.
Figure 7B:
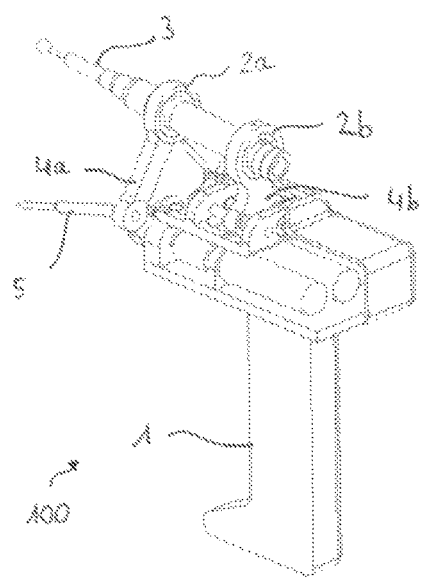

FIGS. 7A-7B illustrate a particular embodiment of a suitable handheld device 100.

Here, the tool 3 is a mill attached to the end-effector 2.

The actuation unit and the end-effector are decomposed into a frontal actuation unit 4a and the corresponding end-effector 2a, and a back actuation unit 4b and the corresponding end-effector 2b.

The handheld device 100 provides three degrees of freedom:
two degrees of freedom are provided by the frontal actuation unit 4a (here, the actuation unit comprises a planar five-bar linkage),
one degree of freedom (feed motion off the pivot point) is provided by the back actuation unit 4b.

The support unit 5 comprises one sharp pin 50 that is connected to the base 1.

The sharp pin 50 is intended to be in contact with the bone adjacent to the bone to be treated.

In use, the user pushes the support unit 5 onto the bone adjacent to the bone to be treated so as to create the partial mechanical link.

Example of Application No 2—Total Knee Arthroplasty (TKA)

In TKA, the tool is used to prepare tibial and femoral bone for implant fixation at a planned position.

The tools generally used in such an intervention are saws and drills.

Typically five planar cuts at the femur and one planar cut at the tibia are done.

According to a first embodiment, the tool is handheld by the user and a tool guide is fixed to the end-effector of the handheld device.

In this way, the tool itself is freely manipulated by the user in one hand but it is guided by the tool guide whose pose is defined in a suitable manner by the system according to the invention, the handheld device being held in the other hand of the user or by an assistant.

Figure 8A:
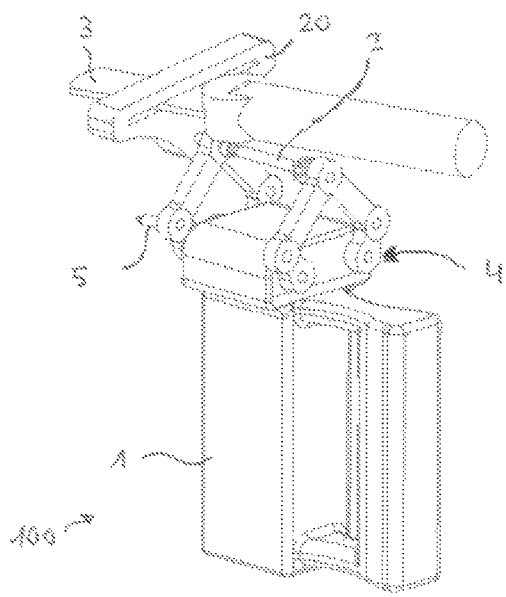
Figure 8B:
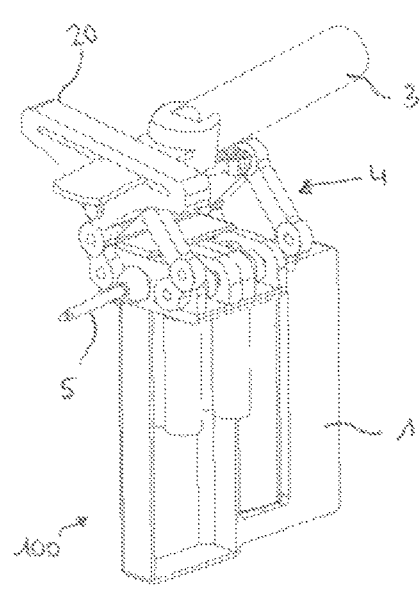

FIGS. 8A-8B shows a particular embodiment of such a handheld device.

The tool guide 20, which is here a saw guide (but it could of course be a drill guide if the tool is a drill), is attached to the end-effector 2.

According to an alternative embodiment, the tool 3 itself is fixed to the end-effector.

A tool guide is not necessary in this case.

FIG. 8C shows a particular embodiment of such a handheld device.

In this case, the tool 3 is a saw that is arranged at the end of the end-effector.

The handheld device provides six degrees of freedom, indicated by arrows:
- two degrees of freedom (XY plane) are provided by the actuation unit to a distal part of the end-effector,
- two degrees of freedom (XY plane) are provided by the actuation unit to a proximal part of the end-effector,
- one degree of freedom (translation along Z axis) is provided by the end-effector,
- one degree of freedom (rotation about Z axis) is provided by the end-effector.

This architecture allows moving the saw in all required directions to carry out total knee arthroplasty.

In the example shown here, the support unit comprises two sharp pins 50 connected to the base 1 that are intended to be in contact with the bone to be treated.

In use, the user pushes the support unit onto the bone to be treated so as to create the partial mechanical link.

Example of Application No 3—Femoro-Acetabular Impingement (FAI)

FIGS. 9A-9B illustrate a handheld device according to a third embodiment of the invention.

Said device is suitable for treatment of FAI, although not limited to this specific application.

In the treatment of FAI, the goal is arthroscopic removal of abnormal shapes, looking like osteophytes, at the femoral head-neck junction and/or the acetabular rim. Currently CT/MRI data are used for preoperative assessment (determination of a planned volume to be removed) and X-ray and arthroscopic images are used for intraoperative orientation. One of the main risks in FAI surgery is over-resection (which would lead to hip instability) or under-resection (which is the most frequent reason for revision surgery). Usually, an arthroscopic approach using three incisions of one cm each is used. The access to the volume to be treated is through arthroscopic portals. The surgeon has to avoid injury of hip blood supply, cartilage and/or capsule during instrument movement via robotic system; a safe area is thus defined for compensation with the planning system.

The parts of the device that fulfill the same function as in the devices described above have the same reference number.

Hence, they will not be described in detail again, apart from their specific features.

The handheld device shown in FIGS. 9A-9B comprises an end-effector 2 that carries a tool 3; here, the tool 3 is a shaver.

Of course, the user could use another tool.

In particular, the surgical tools that are conventionally used in FAI treatment are high-speed mills and shavers.

This handheld device provides three degrees of freedom:
- two degrees of freedom are provided by the actuation unit 4; in the embodiment illustrated here, the actuation unit comprises two spherical five-bar linkages that are synchronously moved by two motor-gear units. Instead of spherical five-bar linkages one could also use planar linkages.
- one degree of freedom (feed motion (z-translation) of the shaver) is provided by the end-effector 2.

The support unit 5 comprises a cushion 54c that provides a contact area with soft tissues of the patient's body (more precisely, with the skin of the hip).

The contact area is as large as possible so as to reduce the pressure applied to the soft tissues to maintain contact between the cushion 54c and the tissues.

The cushion 54c may have a disk shape and be placed on a substantially flat part of the patient's body.

Instead, the cushion may have a ring shape allowing it to be placed around the surgical portal.

The cushion may be fixed to the body of the patient by a strap or by any other means, e.g. by a suction effect, glue or tape.

In this case, the soft tissues of the patient provide a certain damping of the partial mechanical link.

Damping may be further provided by a damping or spring characteristic implemented on the support unit.

Another possibility (in addition to using a pad or vacuum cushion to provide contact between support unit and soft tissue) is to connect the support unit to the trocar which may be used to gain access to the joint.

Although such a cushion is advantageous in that its fixation to the patient's body is not invasive, another possibility (in addition to or instead of) the cushion contacting the soft tissue is to provide a contact with a bone in the vicinity of the part to be treated, e.g. via at least one pin as described for other kinds of surgery.

The at least one pin can be inserted into the patient's body via the portal through which the tool is introduced or via another portal.

REFERENCES

[Kwoh 1988] Kwoh Y S, Hou J, Jonckheere E A, Hayati S: A robot with improved absolute positioning accuracy for CT guided stereotactic brain surgery, IEEE Transactions on Biomedical Engineering, 1988, 35(2):153-160

[Lavallee 1989] Lavallee S: A new system for computer assisted neurosurgery, IEEE Engineering in Medicine and Biology and Society, 1989, 3: 926-927

[Bargar 1998] Bargar W L, Bauer A, Börner M: Primary and revision total hip replacement using the Robodoc system, Clin Orthop Relat Res. 1998 September; (354):82-91

[Prymka 2006] Prymka M, Wu L, Hahne H J, Koebke J, Hassenpflug J: The dimensional accuracy for preparation of the femoral cavity in HIP arthroplasty. A comparison between manual- and robot-assisted implantation of hip endoprosthesis stems in cadaver femurs, Arch Orthop Trauma Surg. 2006 January; 126(1):36-44. Epub 2005 Dec. 8.

[Bach 2002] Bach C M, Winter P, Nogler M, Göbel G, Wimmer C, Ogon M: No functional impairment after Robodoc total hip arthroplasty: gait analysis in 25 patients, Acta Orthop Scand. 2002 August; 73(4):386-91

[Maeso 2010] Maeso S, Reza M, Mayol J A, Blasco J A, Guerra M, Andradas E, Plana M N: Efficacy of the Da Vinci surgical system in abdominal surgery compared with that of laparoscopy: a systematic review and meta-analysis, Ann Surg. 2010 August; 252(2):254-62

[Lieberman 2006] Lieberman I H, Togawa D, Kayanja M M, Reinhardt M K, Friedlander A, Knoller N, Benzel E C: Bone-mounted miniature robotic guidance for pedicle screw and translaminar facet screw placement: Part I—Technical development and a test case result, Neurosurgery. 2006 September; 59(3):641-50

[Plaskos 2005] Plaskos C, Cinquin P, Lavallee S, Hodgson A J: Praxiteles: a miniature bone-mounted robot for minimal access total knee arthroplasty, Int J Med Robot. 2005 December; 1(4):67-79

[Davies 2007] Davies B L, Rodriguez y Baena F M, Barrett A R, Gomes M P, Harris S J, Jakopec M, Cobb J P: Robotic control in knee joint replacement surgery, Proc Inst Mech Eng H. 2007 January; 221(1):71-80

[Yen 2010] Yen P L, Davies B L: Active constraint control for image-guided robotic surgery, Proc Inst Mech Eng H. 2010; 224(5):623-31

[Lonner 2010] Lonner J H, John T K, Conditt M A: Robotic Arm-Assisted UKA Improved Tibial Component Alignment: A Pilot Study, Clin Orthop Relat Res (2010) 468:141-146

[Dorr 2011] Dorr L D, Jones R E, Padgett D E, Pagnano M, Ranawat A S, Trousdale R T: Robotic guidance in total hip arthroplasty: the shape of things to come, Orthopedics. 2011 Sep. 9; 34(9):e652-5

[Cobb 2006] Cobb J, Henckel J, Gomes P, Harris S, Jakopec M, Rodriguez F, Barrett A, Davies B: Hands-on robotic unicompartmental knee replacement: a prospective, randomised controlled study of the acrobot system, J Bone Joint Surg Br. 2006 February; 88(2):188-97

[Strauss 2005] Strauss G, Koulechov K, Richter R, Dietz A, Trantakis C, Lüth T: Navigated control in functional endoscopic sinus surgery, Int J Med Robot, 2005, vol. 1, no. 3, pp. 31-41

[Brisson 2004] Brisson G, Kanade T, DiGioia A, Jaramaz B: Precision Freehand Sculpting of Bone, Proceedings of the 7th International Conference on Medical Image Computing and Computer-Assisted Intervention (MICCAI 2004), vol. 2, pp. 105-112

[Mitchell 2007] Mitchell B, Koo J, Iordachita M, Kazanzides P, Kapoor A, Handa J, Hager G, Taylor R: Development and Application of a New Steady-Hand Manipulator for Retinal Surgery, IEEE International Conference on Robotics and Automation, 2007: 623-629

[Uneri 2010] Uneri A, Balicki M A, Handa J, Gehlbach P, Taylor R H, Iordachita I: New Steady-Hand Eye Robot with Micro-Force Sensing for Vitreoretinal Surgery, Proc IEEE RAS EMBS Int Conf Biomed Robot Biomechatron. 2010 Sep. 1; 2010 (26-29):814-819

[Becker 2011] Becker B C, MacLachlan R A, Hager G D, Riviere C N: Handheld micromanipulation with vision-based virtual fixtures, IEEE International Conference on Robotics and Automation (ICRA), 2011: 4127-4132

[MacLachlan 2012] MacLachlan R A, Becker B C, Cuevas Tabarés J, Podnar G W, Lobes L A, Riviere C N: Micron: An Actively Stabilized Handheld Tool for Microsurgery, IEEE Transactions on Robotics, February 2012, 28(1): 195-212

US 2006/0142657 A1 (Quaid et al.)
WO 2011/133927 A2 (Nikou et al.)
US 2005/0171553 (Schwarz et al.)
US 2012/0143084 (Shoham)
US 2011/0208196 (Radermacher et al.)

The invention claimed is:

1. A surgical system comprising:
(i) a handheld device comprising:
   a base configured to be held in a user's hand,
   an end-effector for mounting a surgical tool or a tool guide for guiding the surgical tool, said surgical tool being configured to treat a planned volume of a part of a patient's body,
   an actuation unit connected to said base and said end-effector for moving said surgical tool or tool guide with respect to the base in order to treat said planned volume,
   a support unit connected to the base or to the end-effector, comprising at least one element configured to make contact with the part to be treated or a region of the patient's body adjacent to the part to be treated so as to provide a partial mechanical link between the base or the end-effector and the part to be treated, the support unit configured so that reaction forces exerted on the partial mechanical link by the part to be treated or the region of the patient's body adjacent to the part to be treated are directed towards a proximal end of the handheld device;
(ii) a tracking unit configured to determine in real time a measured pose of at least one of the tool, the end-effector and the base with respect to the part to be treated;
(iii) a control unit configured to:
   (a) compute in real time an optimized path of the tool or of the end-effector with respect to the base depending on said measured pose as determined by the tracking unit,
   (b) detect whether said optimized path of the tool or of the end-effector can be achieved without changing the pose of the base, and, if this is not the case, determine a possible repositioning of the base with respect to the part to be treated,
   (c) configure the actuation unit so as to move the end-effector according to said computed path, and
   (d) iterate steps (a) to (c) until the planned volume has been treated; and
(iv) a user interface configured to indicate feedback information from the control unit to the user.

2. The system of claim 1, wherein a tool guide is mounted on the end-effector and the support unit comprises the tool guide.

3. The system of claim 1, wherein the support unit comprises at least one sensor for detecting a force exerted by the user on the partial mechanical link and wherein the control unit is configured to check whether said force is greater than a threshold such that the support unit has a minimal damping parameter.

4. The system of claim 1, wherein the support unit comprises at least one damping element, such that said mechanical link created between the base or end-effector and the part to be treated is able to absorb reaction forces exerted by the treated part onto the tool.

5. The system of claim 4, wherein the damping characteristics of said at least one damping element are adjustable.

6. The system of claim 1, wherein the support unit comprises at least one pin having at least one rigid or damped degree of freedom.

7. The system of claim 1, wherein the support unit comprises at least one pad with a surface configured to adhere to patient soft tissue adjacent to the part to be treated.

8. The system of claim 1, wherein the support unit comprises a first portion connected to the base or the end-effector and a second portion intended to at least fit or to be fixed to the part to be treated or to a part of the patient adjacent to the part to be treated.

9. The system of claim 8, wherein the connection between the first and second portions of the support unit includes a hook-and-loop fastener or a magnetic fastener.

10. The system of claim 1, wherein the support unit comprises a hand grip configured to be held by the other user's hand.

11. The system of claim 1, wherein the support unit is articulated with respect to the base.

12. The system of claim 1, wherein the surgical tool is articulated with respect to the end-effector.

13. The system of claim 1, wherein the control unit is configured to stop at least one of the actuation unit and the tool if said control unit detects that the current pose of the tool is outside of the planned volume.

14. The system of claim 1, wherein the support unit comprises a holding arm connected to the base of the handheld device and configured to be connected to a mechanical support.

15. The system of claim 1, further comprising a planning system configured to determine a volume to be treated by the tool.

16. The system of claim 1, wherein a drill guide or a saw guide is comprised in the end-effector or in the support unit and the tool is a drill or a saw that is intended to be moved within the axis or the plane of said guide.

17. The system of claim 1, wherein the surgical tool comprises a saw, a drill, a mill, a shaver or a burr.

18. The system of claim 1, wherein the tracking unit comprises at least one emitter and at least one sensor, said at least one emitter being mounted on the base or on the end-effector and said at least one sensor being adapted to be mounted on the part to be treated.

19. The system of claim 1, wherein the feedback information provided by the user interface comprises an indication of whether said computed path is achievable without changing the pose of at least one of the base and the support unit with respect to the part to be treated, and, if not, an indication of a possible repositioning of at least one of the base and the support unit determined by the control unit.

20. The system of claim 1, further comprising a cable extending from a spring pulley, said cable supporting the base of the handheld device.

21. The system of claim 14, wherein the mechanical support is an operating table.

22. The system of claim 15, wherein the planning system is further configured to determine at least one processing parameter of the tool.

23. A surgical system comprising:
(i) a handheld device comprising:
  a base configured to be held in a user's hand,
  an end-effector for mounting a surgical tool or a tool guide for guiding the surgical tool, said surgical tool being configured to treat a planned volume of a part of a patient's body,
  an actuation unit connected to said base and said end-effector for moving said surgical tool or tool guide with respect to the base in order to treat said planned volume,
  a support unit connected to the base or to the end-effector, comprising at least one element configured to make contact with the part to be treated or a region of the patient's body adjacent to the part to be treated so as to provide a partial mechanical link between the base or the end-effector and the part to be treated, wherein the support unit comprises a first portion connected to the base or the end-effector and a second portion intended to at least fit or to be fixed to the part to be treated or to a part of the patient adjacent to the part to be treated, the connection between the first and second portions of the support unit including a hook-and-loop fastener or a magnetic fastener,
(ii) a tracking unit configured to determine in real time a measured pose of at least one of the tool, the end-effector and the base with respect to the part to be treated,
(iii) a control unit configured to:
  (a) compute in real time an optimized path of the tool or of the end-effector with respect to the base depending on said measured pose as determined by the tracking unit,
  (b) detect whether said optimized path of the tool or of the end-effector can be achieved without changing the pose of the base, and, if this is not the case, determine a possible repositioning of the base with respect to the part to be treated,
  (c) configure the actuation unit so as to move the end-effector according to said computed path, and
  (d) iterate steps (a) to (c) until the planned volume has been treated,
(iv) a user interface configured to indicate feedback information from the control unit to the user.

24. A surgical system comprising:
(i) a handheld device comprising:
  a base configured to be held in a user's hand,
  an end-effector for mounting a surgical tool or a tool guide for guiding the surgical tool, said surgical tool being configured to treat a planned volume of a part of a patient's body, the end-effector defining a longitudinal axis extending therethrough,
  an actuation unit connected to said base and said end-effector for moving said surgical tool or tool guide with respect to the base in order to treat said planned volume,
  a support unit connected to the base or to the end-effector, comprising at least one element configured to make contact with the part to be treated or a region of the patient's body adjacent to the part to be treated so as to provide a partial mechanical link between the base or the end-effector and the part to be treated, wherein the element is off-axis from the longitudinal axis of the end effector;
(ii) a tracking unit configured to determine in real time a measured pose of at least one of the tool, the end-effector and the base with respect to the part to be treated,
(iii) a control unit configured to:
  (a) compute in real time an optimized path of the tool or of the end-effector with respect to the base depending on said measured pose as determined by the tracking unit,
  (b) detect whether said optimized path of the tool or of the end-effector can be achieved without changing the pose of the base, and, if this is not the case, determine a possible repositioning of the base with respect to the part to be treated, (c) configure the actuation unit so as to move the end-effector according to said computed path, and
(d) iterate steps (a) to (c) until the planned volume has been treated,
(iv) a user interface configured to indicate feedback information from the control unit to the user.

25. A surgical system comprising:
(i) a handheld device comprising:
a base configured to be held in a user's hand,
an end-effector for mounting a surgical tool or a tool guide for guiding the surgical tool, said surgical tool being configured to treat a planned volume of a part of a patient's body,
an actuation unit connected to said base and said end-effector for moving said surgical tool or tool guide with respect to the base in order to treat said planned volume,
a support unit connected to the base or to the end-effector, comprising at least one element configured to make contact with the part to be treated or a region of the patient's body adjacent to the part to be treated so as to provide a partial mechanical link between the base or the end-effector and the part to be treated, the support unit configured so that the element does not obstruct the path of the end effector;
(ii) a tracking unit configured to determine in real time a measured pose of at least one of the tool, the end-effector and the base with respect to the part to be treated,
(iii) a control unit configured to:
(a) compute in real time an optimized path of the tool or of the end-effector with respect to the base depending on said measured pose as determined by the tracking unit,
(b) detect whether said optimized path of the tool or of the end-effector can be achieved without changing the pose of the base, and, if this is not the case, determine a possible repositioning of the base with respect to the part to be treated,
(c) configure the actuation unit so as to move the end-effector according to said computed path, and
(d) iterate steps (a) to (c) until the planned volume has been treated,
(iv) a user interface configured to indicate feedback information from the control unit to the user.

26. The system of claim 25, wherein the support unit comprises at least one resilient damping element.

27. The system of claim 26, wherein the resilient damping element comprises a spring.

28. A surgical system comprising:
(i) a handheld device comprising:
a base configured to be held in a user's hand,
an end-effector for mounting a surgical tool or a tool guide for guiding the surgical tool, said surgical tool being configured to treat a planned volume of a part of a patient's body,
an actuation unit connected to said base and said end-effector for moving said surgical tool or tool guide with respect to the base in order to treat said planned volume,
a support unit connected to the base or to the end-effector, comprising at least one element configured to make contact with the part to be treated or a region of the patient's body adjacent to the part to be treated so as to provide a partial mechanical link between the base or the end-effector and the part to be treated,
(ii) a tracking unit configured to determine in real time a measured pose of at least one of the tool, the end-effector and the base with respect to the part to be treated;
(iii) a control unit configured to:
(a) compute in real time an optimized path of the tool or of the end-effector with respect to the base depending on said measured pose as determined by the tracking unit,
(b) detect whether said optimized path of the tool or of the end-effector can be achieved without changing the pose of the base, and, if this is not the case, determine a possible repositioning of the base with respect to the part to be treated,
(c) configure the actuation unit so as to move the end-effector according to said computed path, and
(d) iterate steps (a) to (c) until the planned volume has been treated; and
(iv) a user interface configured to indicate feedback information from the control unit to the user;
wherein the support unit comprises at least one sensor for detecting a force exerted by the user on the partial mechanical link and wherein the control unit is configured to check whether said force is greater than a threshold such that the support unit has a minimal damping parameter.

29. A surgical system comprising:
(i) a handheld device comprising:
a base configured to be held in a user's hand,
an end-effector for mounting a surgical tool or a tool guide for guiding the surgical tool, said surgical tool being configured to treat a planned volume of a part of a patient's body,
an actuation unit connected to said base and said end-effector for moving said surgical tool or tool guide with respect to the base in order to treat said planned volume,
a support unit connected to the base or to the end-effector, comprising at least one element configured to make contact with the part to be treated or a region of the patient's body adjacent to the part to be treated so as to provide a partial mechanical link between the base or the end-effector and the part to be treated,
(ii) a tracking unit configured to determine in real time a measured pose of at least one of the tool, the end-effector and the base with respect to the part to be treated;
(iii) a control unit configured to:
(a) compute in real time an optimized path of the tool or of the end-effector with respect to the base depending on said measured pose as determined by the tracking unit,
(b) detect whether said optimized path of the tool or of the end-effector can be achieved without changing the pose of the base, and, if this is not the case, determine a possible repositioning of the base with respect to the part to be treated,
(c) configure the actuation unit so as to move the end-effector according to said computed path, and
(d) iterate steps (a) to (c) until the planned volume has been treated; and
(iv) a user interface configured to indicate feedback information from the control unit to the user;
wherein the support unit comprises at least one pad with a surface configured to adhere to patient soft tissue adjacent to the part to be treated.

30. A surgical system comprising:
(i) a handheld device comprising:
   a base configured to be held in a user's hand,
   an end-effector for mounting a surgical tool or a tool guide for guiding the surgical tool, said surgical tool being configured to treat a planned volume of a part of a patient's body,
   an actuation unit connected to said base and said end-effector for moving said surgical tool or tool guide with respect to the base in order to treat said planned volume,
   a support unit connected to the base or to the end-effector, comprising at least one element configured to make contact with the part to be treated or a region of the patient's body adjacent to the part to be treated so as to provide a partial mechanical link between the base or the end-effector and the part to be treated,
(ii) a tracking unit configured to determine in real time a measured pose of at least one of the tool, the end-effector and the base with respect to the part to be treated;
(iii) a control unit configured to:
   (a) compute in real time an optimized path of the tool or of the end-effector with respect to the base depending on said measured pose as determined by the tracking unit,
   (b) detect whether said optimized path of the tool or of the end-effector can be achieved without changing the pose of the base, and, if this is not the case, determine a possible repositioning of the base with respect to the part to be treated,
   (c) configure the actuation unit so as to move the end-effector according to said computed path,
   (d) iterate steps (a) to (c) until the planned volume has been treated; and
(iv) a user interface configured to indicate feedback information from the control unit to the user; and
(v) a cable extending from a spring pulley, said cable supporting the base of the handheld device.

31. The system of claim 1, wherein the partial mechanical link is configured to be non-invasive as the end effector is moved along the computed path.

32. The system of claim 1, wherein the surgical tool extends distally beyond the distal end of the partial mechanical link.

\* \* \* \* \*